(12) United States Patent
Kanemasa et al.

(10) Patent No.: US 10,363,397 B2
(45) Date of Patent: Jul. 30, 2019

(54) CATHETER, CATHETER MANIPULATION PART, AND CATHETER MANUFACTURING METHOD

(71) Applicant: SUMITOMO BAKELITE CO., LTD., Shinagawa-ku (JP)

(72) Inventors: Kenichi Kanemasa, Akita (JP); Shinetsu Harata, Akita (JP); Yoshihiro Abe, Akita (JP); Hayao Tanaka, Akita (JP); Masao Ikeda, Akita (JP); Keiji Kamada, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 551 days.

(21) Appl. No.: 14/779,480

(22) PCT Filed: Mar. 26, 2014

(86) PCT No.: PCT/JP2014/058596
§ 371 (c)(1),
(2) Date: Sep. 23, 2015

(87) PCT Pub. No.: WO2014/157366
PCT Pub. Date: Oct. 2, 2014

(65) Prior Publication Data
US 2016/0051796 A1 Feb. 25, 2016

(30) Foreign Application Priority Data

Mar. 28, 2013 (JP) ................. 2013-069528

(51) Int. Cl.
*A61M 25/01* (2006.01)
*A61M 25/00* (2006.01)
*B65B 55/14* (2006.01)

(52) U.S. Cl.
CPC .... *A61M 25/0136* (2013.01); *A61M 25/0009* (2013.01); *A61M 25/0147* (2013.01);
(Continued)

(58) Field of Classification Search
CPC ............... A61M 25/0147; A61B 34/71; A61B 2034/301; A61B 2034/715
See application file for complete search history.

(56) References Cited

U.S. PATENT DOCUMENTS 5,195,968 A * 3/1993 Lundquist ......... A61M 25/0136
600/585
8,702,783 B2 4/2014 Yamashita
(Continued)

FOREIGN PATENT DOCUMENTS

CN 102271627 A 12/2011
EP 0 980 693 A 2/2000
(Continued)

OTHER PUBLICATIONS

International Search Report dated Jul. 8, 2014 for PCT/JP2014/058596 filed on Mar. 26, 2014.

*Primary Examiner* — Nathan R Price
*Assistant Examiner* — John A Doubrava
(74) *Attorney, Agent, or Firm* — Oblon, McClelland, Maier & Neustadt, L.L.P.

(57) ABSTRACT

A catheter of the invention includes an elongated flexible tubular main body; a plurality of manipulation wires inserted through the tubular main body and having tips connected to a distal part of the tubular main body; a manipulation-part main body provided at a base end of the tubular main body; and a bending manipulation part. The bending manipulation part has an engagement part engaging with base ends of the manipulation wires, and individually applies pulling force to the plurality of manipulation wires through pulling opera-
(Continued)

tions so as to bend the distal part of the tubular main body. The bending manipulation part is provided so as to be movable with respect to the manipulation-part main body. The path lengths of the plurality of manipulation wires from the tips thereof to the engagement part are simultaneously increased or decreased when the bending manipulation part and the manipulation-part main body move relative to each other.

18 Claims, 12 Drawing Sheets

(52) U.S. Cl.
CPC ............ *B65B 55/14* (2013.01); *A61M 25/005* (2013.01); *A61M 25/0045* (2013.01); *A61M 25/0097* (2013.01); *A61M 25/0108* (2013.01)

(56) References Cited

U.S. PATENT DOCUMENTS

| 2007/0010801 | A1 | 1/2007 | Chen et al. |
| 2008/0312506 | A1* | 12/2008 | Spivey ............... A61B 1/00133 600/149 |
| 2012/0022635 | A1 | 1/2012 | Yamashita |
| 2014/0148759 | A1* | 5/2014 | Macnamara ...... A61M 25/0147 604/95.04 |

FOREIGN PATENT DOCUMENTS

| EP | 1 803 481 A2 | 7/2007 |
| JP | 2008-502433 A | 1/2008 |
| JP | 2010-253125 A | 11/2010 |
| WO | 2005/123169 A1 | 12/2005 |
| WO | WO 2007/002545 A1 | 1/2007 |

* cited by examiner

CATHETER, CATHETER MANIPULATION PART, AND CATHETER MANUFACTURING METHOD

TECHNICAL FIELD

The present invention relates to a catheter, a catheter manipulation part, and a catheter manufacturing method.

Priority is claimed on Japanese Patent Application No. 2013-069528, filed Mar. 28, 2013, the content of which is incorporated herein by reference.

BACKGROUND ART

Catheters capable of pulling manipulation wires to perform bending manipulation of a distal part have been suggested. It is possible to bend the distal part bent inside a body cavity or at a branch point, thereby selecting an insertion direction.

PTL 1 discloses a catheter including a manipulating mechanism referred to as a dial part. Two manipulation wires branching from a tubular main body are mounted around the dial part in opposite directions and fixed thereto. The tubular main body (sheath) of the catheter is pulled out to a base end side of a manipulation-part main body through a lower part of the dial part, and a position adjusting mechanism and a hub connector are provided in the tubular main body. The position adjusting mechanism is a mechanism that moves the hub connector and the tubular main body forward and backward relative to the manipulation-part main body and the manipulation wires, thereby adjusting the tension of the manipulation wires. More specifically, the position adjusting mechanism is capable of being screwed in a forward-backward direction with respect to the manipulation-part main body, and when the position adjusting mechanism is moved forward with respect to the manipulation-part main body, a distal end of the tubular main body moves forward. Since tips of the manipulation wires are fixed to the distal end of the tubular main body, as the position adjusting mechanism moves forward, the tips of the manipulation wires also move forward. Meanwhile, base ends of the manipulation wires are fixed to the dial part of the manipulation part. For this reason, as the position adjusting mechanism moves forward, loosening of the manipulation wires is removed or the tension thereof is increased. On the contrary, when the position adjusting mechanism is moved backward with respect to the manipulation-part main body, the tips of the manipulation wires are moved backward together with the distal end of the tubular main body. Accordingly, the manipulation wires are loosened or the tension thereof is decreased.

The tubular main body of the catheter of PTL 1 is formed by combining an inner layer and an outer layer made of resin, and a metallic reinforcing layer that reinforces these layers. The reinforcing layer is formed by braiding metallic thin wires in the shape of a mesh. Meanwhile, in order to obtain high breaking strength, a metallic single wire or a metallic stranded wire is used for the manipulation wires.

[PTL 1] Japanese Unexamined Patent Application, First Publication No. 2010-253125

SUMMARY OF INVENTION

The tubular main body is formed by combining resin and metal, and the manipulation wires are made of metal. For this reason, the coefficients of linear expansion and the swelling coefficients of the tubular main body and the manipulation wires are greatly different from each other. Specifically, the coefficient of thermal expansion and the swelling coefficients of the tubular main body are about 10 times greater than those of the manipulation wires. For this reason, the present inventors found out that, when the heat environment or the humidity environment of the catheter fluctuates after assembling and forming of the catheter, new problems occur in that large loads are applied to the manipulation wires or the tubular main body, and the manipulation wires break or the tubular main body is plastically bent.

As a final step of the manufacturing of the catheter, sterilization processing is performed after both ends of the manipulation wires are fixed. Although various methods are present as the sterilization processing, a typical method is a heating and sterilizing method for replacing the air inside a sterilization bag, in which a catheter is housed, with sterilization gases, such as ethylene oxide gas, under a heating atmosphere of about 50° C. Under this heating atmosphere, the thermal expansion of the tubular main body is greater than that of the manipulation wires, and the tubular main body further elongates from a state where the manipulation wires are tightly stretched without being loosened. For this reason, tension is applied to the manipulation wires in a pulling direction, and compressive force in the direction of an axial center is applied to the tubular main body as the resistance of the tension. Here, in the case of a catheter with a relatively fine diameter, particularly, a micro catheter with a fine diameter capable of being inserted into a peripheral blood vessel as in PTL 1, the manipulation wires are very thin and the tubular main body is very flexible. For this reason, due to the thermal expansion of the catheter under the heating atmosphere, the manipulation wires easily break due to the above tension, and the tubular main body is easily bent and plastically deformed in a lateral direction due to the above compressive force.

Such thermal expansion is a problem that may occur under various environments after the assembling or packaging of catheters, such as transportation environments in summer, as well as at the time of the heating and sterilization.

In contrast, in the catheter of PTL 1, the position adjusting mechanism is moved backward with respect to a manipulation-part main body, so that the distal end of the tubular main body can be moved backward and the manipulation wires can be loosened. Therefore, by sufficiently moving the position adjusting mechanism backward in advance under a normal temperature atmosphere, it is possible to avoid a situation in which tension is generated in the manipulation wires even when thermal expansion of the catheter has occurred. Then, by moving the position adjusting mechanism forward when the catheter is used, the tubular main body can be moved forward with respect to the manipulation-part main body, and the loosening of the manipulation wires can be removed.

However, when the tubular main body is compulsorily moved forward with respect to the manipulation-part main body after heating and sterilizing or after transportation in a heating environment, there are concerns that new problems occur in the quality of the catheter such that the resin layer of the tubular main body is deformed or a hydrophilic layer of an outermost layer is damaged. Additionally, the above problems occur similarly even in so-called swelling deformation in which the tubular main body expands more than the manipulation wires under a humid atmosphere, as well as the heating.

The invention has been made in view of the above problems, and an object thereof is to provide a high-quality catheter without damaging manipulation wires or a tubular main body under an environment of heating or swelling after the assembly of the catheter. Additionally, the invention provides a catheter manipulation part and a catheter manufacturing method together.

According to the invention, there is provided a catheter including an elongated flexible tubular main body; a plurality of manipulation wires inserted through the tubular main body and having tips connected to a distal part of the tubular main body; a manipulation-part main body provided at a base end of the tubular main body; and a bending manipulation part having an engagement part engaging with base ends of the manipulation wires, and individually applying pulling force to the plurality of manipulation wires through pulling operations so as to bend the distal part of the tubular main body. The bending manipulation part is provided so as to be movable with respect to the manipulation-part main body. The path lengths of the plurality of manipulation wires from the tips thereof to the engagement part are simultaneously increased or decreased when the bending manipulation part and the manipulation-part main body move relative to each other.

Additionally, according to the invention, there is provided a catheter manipulation part used for a catheter including an elongated flexible tubular main body, and a plurality of manipulation wires inserted through the tubular main body and having tips connected to a distal part of the tubular main body, the distal part of the tubular main body being bent when pulling the manipulation wires. The catheter manipulation part includes a manipulation-part main body mounted on a base end of the tubular main body; and a bending manipulation part including an engagement part engaging with base ends of the manipulation wires, and individually applying pulling force to the plurality of manipulation wires through pulling operations. The bending manipulation part is provided so as to be movable with respect to the manipulation-part main body. The path lengths of the plurality of manipulation wires from the tips thereof to the engagement part are simultaneously increased or decreased when the bending manipulation part and the manipulation-part main body move relative to each other.

Additionally, according to the invention, there is provided a catheter manufacturing method for manufacturing the above catheter including a step of preparing the catheter in which the bending manipulation part is at the retracted position; a step of housing the catheter in a sterilizing package to heat and sterilize the catheter; and a step of causing the bending manipulation part in the heated and sterilized catheter to transit from the retracted position to the manipulation position, thereby removing some or all of loosening of the manipulation wires.

According to the invention, the bending manipulation part having the engagement part engaging with the base ends of the manipulation wires is provided so as to be movable with respect to the manipulation-part main body, and the path lengths of the manipulation wires from the tips thereof to the engagement part are simultaneously increased or decreased when the bending manipulation part and the manipulation-part main body move relative to each other. For this reason, by moving the bending manipulation part relative to the manipulation-part main body, the manipulation wires can be loosened or the loosening thereof can be removed. Accordingly, the problem of damage to the manipulation wires or the tubular main body resulting from heating or swelling can be solved without moving the tubular main body with respect to the manipulation-part main body or by reducing an amount by which the tubular main body is moved with respect to the manipulation-part main body.

According to the catheter, the catheter manipulation part, and the catheter manufacturing method of the invention, a high-quality catheter is provided without damaging the manipulation wires or the tubular main body under an environment of heating or swelling after the assembly of the catheter.

BRIEF DESCRIPTION OF DRAWINGS

FIG. 14(a) illustrates the catheter manipulation part when the bending manipulation part is at the retracted position, and FIG. 14(b) illustrates the catheter manipulation part when the bending manipulation part is at the manipulation position.

DESCRIPTION OF EMBODIMENTS

Figure 1:
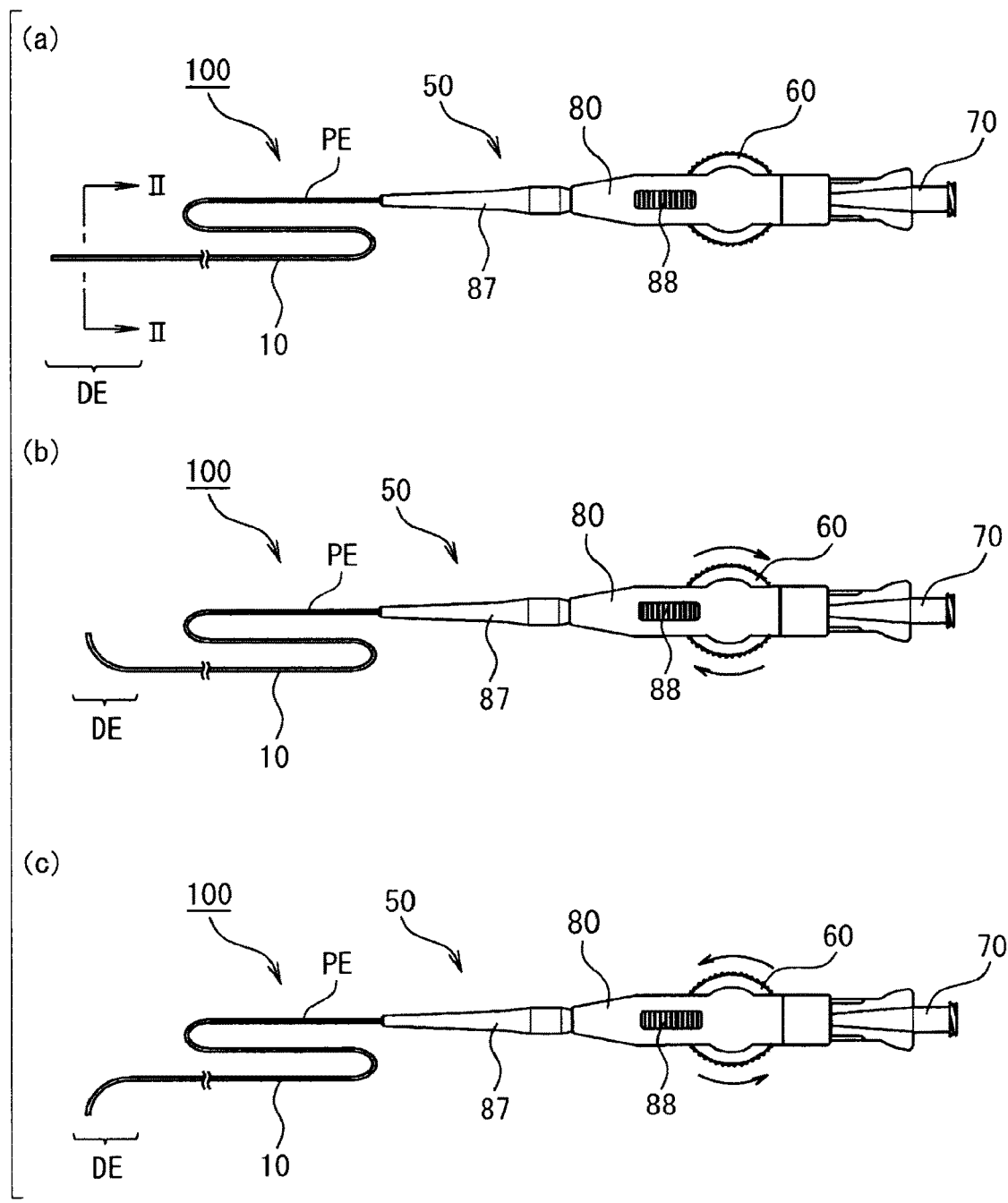
FIG. 1(a) is a plan view of a catheter of a first embodiment of the invention.
FIG. 1(b) is a plan view of the catheter illustrating a state where a bending manipulation part has been manipulated in one direction.
FIG. 1(c) is a plan view of the catheter illustrating a state where the bending manipulation part has been manipulated in the other direction.

Hereinafter, embodiments of the invention will be described with reference to the drawings. In addition, in all the drawings, the same constituent elements will be designated by the same reference numerals, and the description thereof will be appropriately omitted. Additionally, in order to make characterizing portions clearly seen, in all the drawings, scales do not necessarily coincide with actual aspects and scales also vary between each of the drawings.

First Embodiment

First, the outline of a catheter 100 of the present embodiment will be described.

FIG. 1(a) is a plan view illustrating an overall configuration of the catheter 100 of the present embodiment. FIG. 1(b) is a plan view of the catheter 100 illustrating a state where a bending manipulation part 60 has been manipulated in one direction (in a clockwise direction in this drawing). FIG. 1(c) is a plan view of the catheter 100 illustrating a state where the bending manipulation part 60 has been manipulated in the other direction (in a counterclockwise direction in this drawing).

Figure 2:
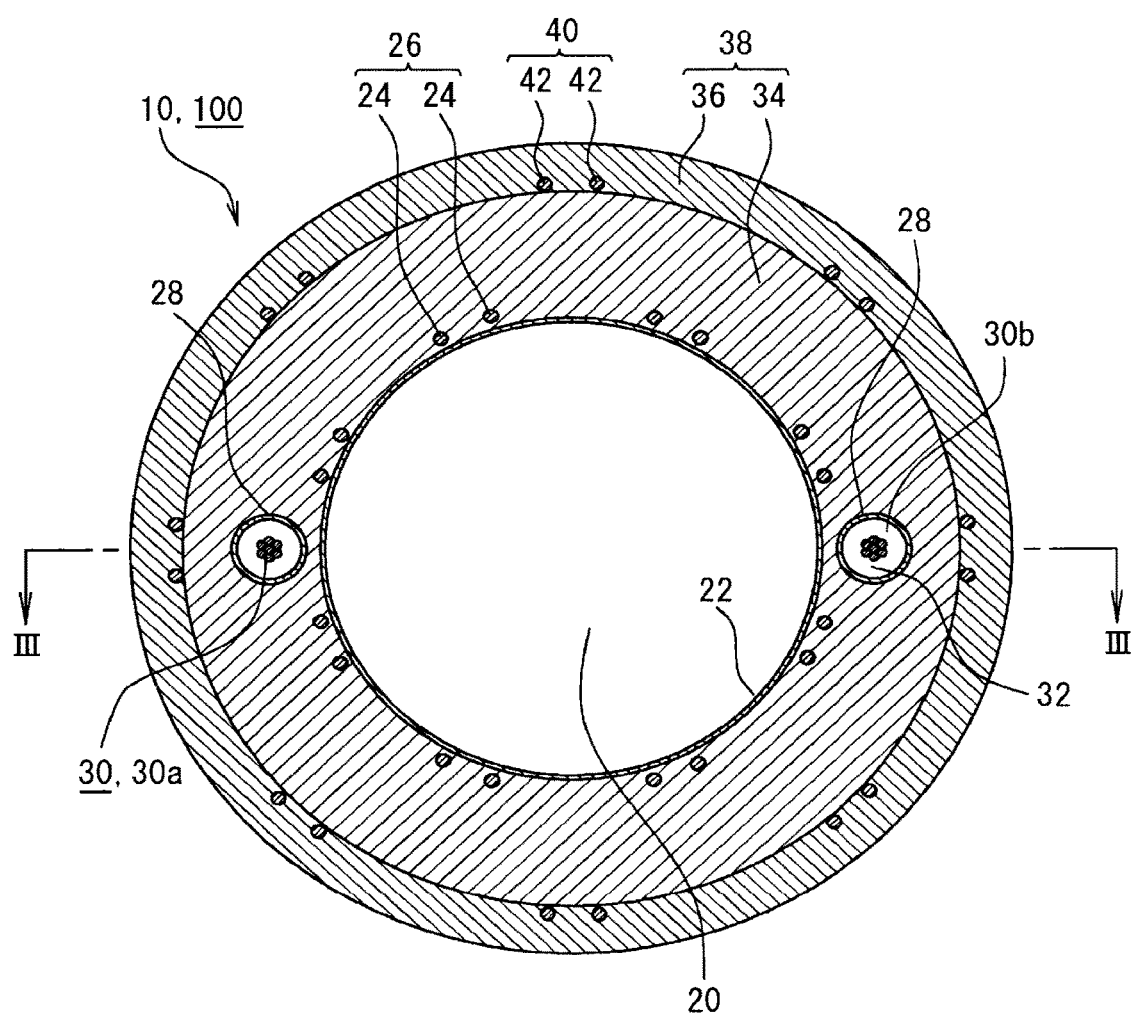
FIG. 2 is a cross-sectional view of the catheter and is a sectional view along line II-II of FIG. 1(a).

FIG. 2 is a cross-sectional view of the catheter 100 and is a sectional view along line II-II of FIG. 1(a).

Figure 3:
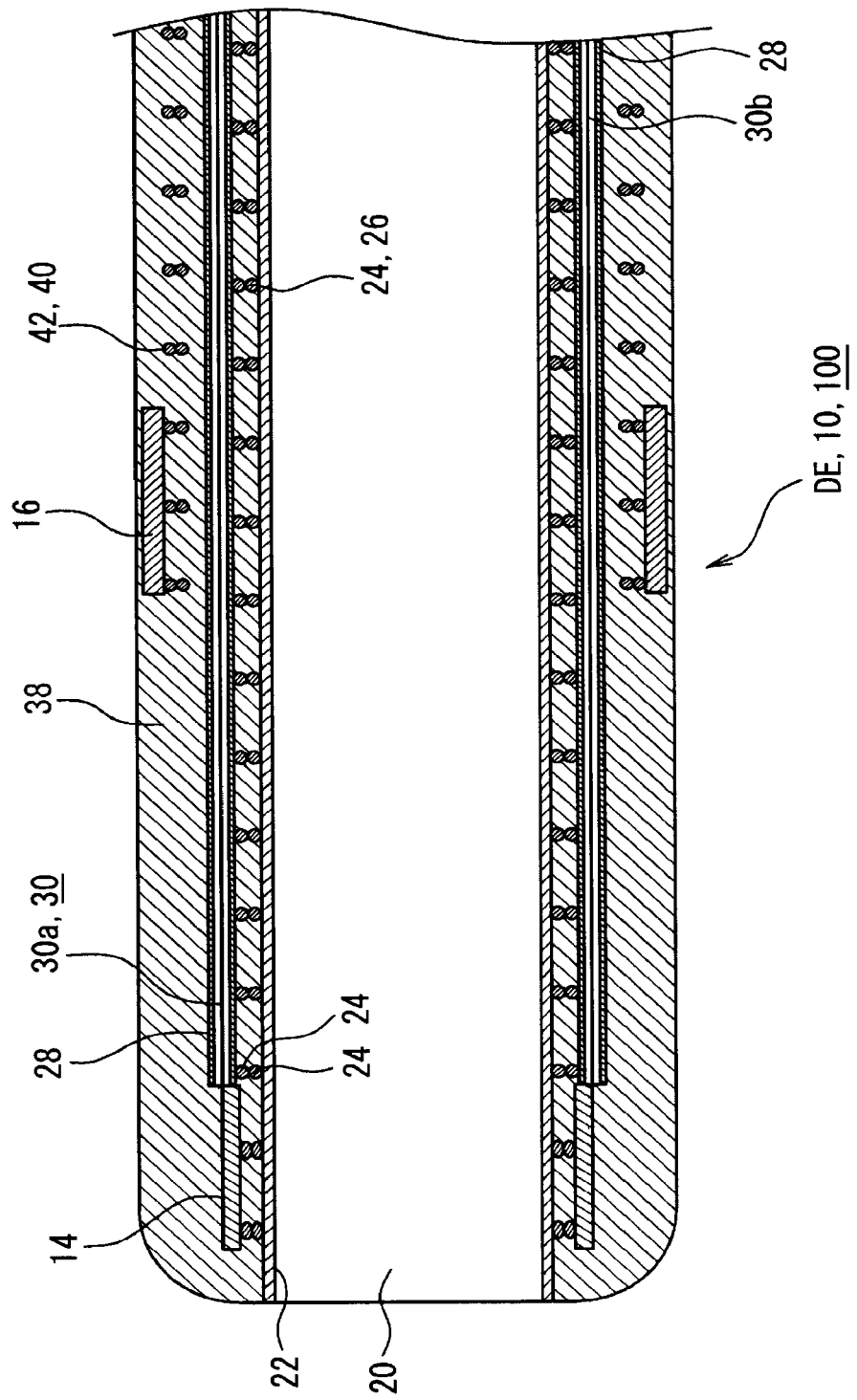
FIG. 3 is a longitudinal sectional view of a distal part of the catheter, and is a sectional view along line III-III of FIG. 2.

FIG. 3 is a longitudinal sectional view of a distal part DE of the catheter 100, and is a sectional view along line of FIG. 2.

The catheter 100 includes an elongated flexible tubular main body 10, a plurality of manipulation wires 30a and 30b that are inserted through the tubular main body 10 and have tips connected to a distal part DE of the tubular main body 10, a manipulation-part main body 80 that is provided at a base end PE of the tubular main body 10, and a bending manipulation part 60.

The bending manipulation part 60 has engagement parts 66 (refer to FIGS. 8 and 9) engaging with base ends of the manipulation wires 30a and 30b, and individually applies pulling force to the plurality of manipulation wires 30a and 30b through pulling manipulations to bend the distal part DE of the tubular main body 10. The bending manipulation part 60 is provided so as to be movable with respect to the manipulation-part main body 80.

The catheter 100 of the present embodiment is characterized in that the path lengths of the plurality of manipulation wires 30a and 30b from the tips thereof to the engagement parts 66 are simultaneously increased or decreased by moving the bending manipulation part 60 and the manipulation-part main body 80 relative to each other.

The catheter manipulation part 50 of the present embodiment is used for the catheter 100, that is, the catheter 100 which includes the tubular main body 10 and the manipulation wires 30a and 30b and in which the distal part DE of the tubular main body 10 is bent by pulling the manipulation wires 30a and 30b. Hereinafter, the catheter manipulation part is abbreviated as a "manipulation part".

The manipulation part 50 includes the manipulation-part main body 80 on which the base end PE of the tubular main body 10 is mounted, and the bending manipulation part 60 that has the engagement parts 66 (refer to FIGS. 8 and 9) engaging with the base ends of the manipulation wires 30a and 30b, and individually applies pulling force to the plurality of manipulation wires 30a and 30b through pulling manipulations. The bending manipulation part 60 is provided so as to be movable with respect to the manipulation-part main body 80.

Figure 9:
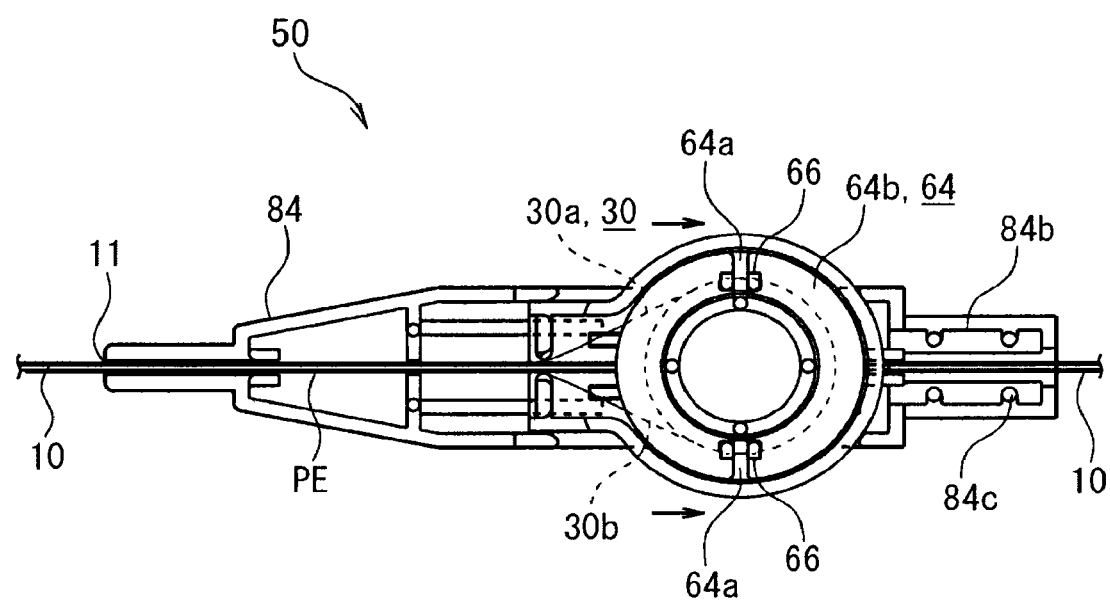
FIG. 9 is a plan view illustrating the state of the manipulation wires when the bending manipulation part is at the manipulation position.

In the manipulation part 50 of the present embodiment, the path lengths from the base end PE of the tubular main body 10 to the engagement parts 66 are increased or decreased by moving the bending manipulation part 60 and the manipulation-part main body 80 relative to each other. Here, the path lengths from the base end PE of the tubular main body 10 to the engagement parts 66, as illustrated in FIG. 9, means the lengths until the manipulation wires 30 that are stretched without loosening reach the engagement parts 66, from a pull-in position 11 of the tubular main body 10 with respect to the manipulation-part main body 80 (lower main body 84).

The manipulation-part main body 80 is a housing that a user grips with his/her hand. The base end PE of the tubular main body 10 is introduced into the manipulation-part main body 80 after being protected by a tubular protector 87.

The manipulation part 50 includes a hub connector 70, in addition to the manipulation-part main body 80 and the bending manipulation part 60. The hub connector 70 is mounted on a rear end of the manipulation-part main body 80. A portion nearest to the base end of the tubular main body 10 is connected to the hub connector 70, and communicates therewith, and a syringe (not illustrated) is mounted from the rear (the right of FIG. 1(a)) of the hub connector 70. By injecting a medicinal solution or the like into the hub connector 70 using the syringe, the medicinal solution or the like can be supplied into a patient's body cavity via a main lumen 20 (refer to FIGS. 2 and 3).

Next, the outline of the operation of the catheter 100 will be described.

As illustrated in FIGS. 2 and 3, the manipulation wires 30a and 30b are inserted through the tubular main body 10. The manipulation wires 30a and 30b are pulled out laterally from the tubular main body 10 inside the manipulation-part main body 80, and are directly or indirectly coupled to the bending manipulation part 60 (refer to FIGS. 8 and 9).

The bending manipulation part 60 of the present embodiment is rotatable with respect to the manipulation-part main body 80. In addition, in the present embodiment, the rotation and turning are not distinguished from each other. When the bending manipulation part 60 is rotated in one direction, the first manipulation wire 30a is tensioned and the second manipulation wire 30b is loosened, and when the bending manipulation part 60 is rotated in the other direction, the second manipulation wire 30b is tensioned, and the first manipulation wire 30a is loosened. The pulled manipulation wire 30a or 30b bends the distal part DE of the catheter 100.

Specifically, when the bending manipulation part 60 is rotated in one direction (clockwise direction) as illustrated in FIG. 1(b), the first manipulation wire 30a (refer to FIG. 3) is pulled to a base end side, and the distal part DE of the tubular main body 10 is bent. When the bending manipulation part 60 is rotated in the other direction (counterclockwise direction) around its rotational axis as illustrated in FIG. 1(c), the second manipulation wire 30b is pulled to the base end side, and the distal part DE is bent in an opposite direction. In this way, the distal part DE of the catheter 100 can be selectively bent by selectively pulling the two manipulation wires 30a and 30b in a first direction or in a second direction included in the same plane.

Here, the tubular main body 10 being bent includes an aspect in which the tubular main body 10 is bent in a "V-shape", and an aspect in which the tubular main body is bent like a bow.

Here, when there is only one manipulation wire 30, the above-described problem of thermal expansion can be avoided when the manipulation part 50 is manipulated to loosen the manipulation wire 30. When the catheter 100 is used, the manipulation part 50 may be operated so as to remove the loosening of the manipulation wire 30, and may locate the manipulation wire at an initial position thereof. In contrast, as in the present embodiment, in the case of the manipulation part 50 in which, when one of the plurality of manipulation wires 30a and 30b is loosened, the other manipulation wire is pulled, a mechanism for simultaneously loosening the plurality of manipulation wires 30a and 30b is required. The present embodiment realizes this through the transition of the bending manipulation part 60.

A peripheral surface of the bending manipulation part 60 (dial manipulation part 61: refer to FIGS. 4 to 7) is formed with a concavo-convex engagement part. The manipulation-part main body 80 is provided with a lock slider 88 that slides so as to be capable of being brought close to and separated from the bending manipulation part 60. When the bending manipulation part 60 is made to slide toward the lock slider 88, the bending manipulation part and the lock slider engage with each other, and the rotation of the bending manipulation part 60 is restricted. Accordingly, the bending state of the catheter 100 can be held by manipulating the lock slider 88 in the state of FIG. 1(*b*) or 1(*c*) where the distal part DE of the catheter 100 is bent, thereby restricting the rotation of the bending manipulation part 60.

Next, the detailed structure of the catheter 100 will be described. The catheter 100 of the present embodiment is an intravascular catheter that is used after the tubular main body 10 is inserted into a blood vessel.

<Tubular Main Body>

The structure of the tubular main body 10 will be described with reference to FIGS. 2 and 3.

The tubular main body 10 is also referred to as a sheath, and is a hollow tubular elongated member through which the main lumen 20 is formed as a through-hole. The tubular main body 10 is formed with an external diameter and a length such that the tubular main body can be advanced into any one of eight sub-sections of the liver. The external diameter of the distal part DE of the tubular main body 10 is less than 1 mm, and the catheter 100 of the present embodiment is a micro catheter capable of being inserted into a peripheral blood vessel.

The tubular main body 10 has the main lumen 20, and a plurality of sub-lumens 32 through which the plurality of manipulation wires 30a and 30b are inserted with smaller diameters than the main lumen 20.

The tubular main body 10 includes a wire reinforcing layer 26 that is formed by winding a reinforcing wire 24 around the main lumen 20, resinous sub-tubes 28 that are arranged outside the wire reinforcing layer 26 and demarcate the sub-lumens 32 having smaller diameters than the main lumen 20, and a resinous outer layer 38 that sheaths the wire reinforcing layer 26 and the sub-tubes 28.

The tubular main body 10 has a stacked structure. The tubular main body 10 is configured such that an inner layer 22, a first outer layer 34, and a second outer layer 36 are stacked sequentially from an internal diameter side with the main lumen 20 as a center. An outer surface of the second outer layer 36 is formed with a hydrophilic layer (not illustrated). The inner layer 22, the first outer layer 34, and the second outer layer 36 are made of flexible resin materials, are annular, and have substantially uniform thicknesses. The first outer layer 34 and the second outer layer 36 may be altogether referred to the outer layer 38.

The inner layer 22 is an innermost layer of the tubular main body 10, and the main lumen 20 is demarcated by an inner wall surface of the inner layer. Although the cross-sectional shape of the main lumen 20 is not particularly limited, the cross-sectional shape is circular in the present embodiment. In the case of the main lumen 20 having a circular cross-section, the diameter of the main lumen may be uniform in the longitudinal direction of the tubular main body 10, or may be different depending on the positions thereof in the longitudinal direction. For example, a partial or total length region of the tubular main body 10 may have a tapered shape in which the diameter of the main lumen 20 is continuously increased from the tip toward the base end.

The materials of the inner layer 22 may include, for example, fluorine-based thermoplastic polymer materials. The fluorine-based thermoplastic polymer materials can include, specifically, polytetrafluoroethylene (PTFE), polyvinylidene fluoride (PVDF), and perfluoroalkoxy fluororesin (PFA). By making the inner layer 22 of such fluorine-based polymer materials, the delivery performance when supplying a medicinal solution or the like through the main lumen 20 becomes excellent. Additionally, when a guide wire is inserted through the main lumen 20, the sliding resistance of the guide wire is reduced.

The wire reinforcing layer 26 and the sub-tubes 28 are provided inside the first outer layer 34 corresponding to an inside layer of the outer layer 38 sequentially from the internal diameter side. The second reinforcing layer 40 is provided inside the second outer layer 36 corresponding to an outside layer of the outer layer 38. The second reinforcing layer 40 is in contact with an outer surface of the first outer layer 34. The wire reinforcing layer 26 and the second reinforcing layer 40 are arranged coaxially with the tubular main body 10. The second reinforcing layer 40 is spaced apart from the wire reinforcing layer 26 and the sub-tubes 28 so as to surround the peripheries of the wire reinforcing layer and the sub-tubes.

Thermoplastic polymer materials can be used as the material of the outer layer 38. This thermoplastic polymer materials may include nylon elastomer, such as polyimide (PI), polyamide imide (PAI), polyethylene terephthalate (PET), polyethylene (PE), polyamide (PA), polyamide elastomer (PAE), or polyether block amide (PEBA), polyurethane (PU), ethylene-vinyl acetate resin (EVA), polyvinyl chloride (PVC), and polypropylene (PP).

Inorganic fillers may be mixed for the outer layer 38. As the inorganic fillers, contrast media such as barium sulfate or basic bismuth carbonate, can be exemplified. By mixing the contrast media for the outer layer 38, the X-ray contrast performance of the tubular main body 10 within a body cavity can be improved.

The first outer layer 34 and the second outer layer 36 are made of the same kind of resin materials or different kinds of resin materials. Although a boundary surface between the first outer layer 34 and the second outer layer 36 is clearly seen in FIG. 2, the invention is not limited to this. When the first outer layer 34 and the second outer layer 36 are made of the same kind of resin materials, the boundary surface between both of the layers may be united in complete harmony. That is, the outer layer 38 of the present embodiment may be constituted as a multilayer in which the first outer layer 34 and the second outer layer 36 are distinguishable from each other, or may be constituted of a monolayer in which the first outer layer 34 and the second outer layer 36 may be integrated with each other. In FIG. 3, the first outer layer 34 and the second outer layer 36 are simplified and are collectively illustrated as the outer layer 38.

The hydrophilic layer formed on the outer surface of the second outer layer 36 constitutes an outermost layer of the catheter 100 (not illustrated). The hydrophilic layer may be formed over the entire length of the tubular main body 10, or may be formed only in a partial length region on the tip side including the distal part DE. The hydrophilic layer is made of, for example, maleic anhydride-based polymers, such as polyvinyl alcohol (PVA) and its copolymers, or hydrophillic resin materials, such as polyvinyl pyrrolidone.

The wire reinforcing layer 26 is a protective layer that is provided closer to the internal diameter side than the manipulation wires 30 in the tubular main body 10 to protect the inner layer 22. As the wire reinforcing layer 26 is present on the internal diameter side of the manipulation wires 30, a situation is prevented in which the manipulation wires 30 break the first outer layer 34 and the inner layer 22 and are exposed to the main lumen 20.

The wire reinforcing layer 26 is formed by winding the reinforcing wire 24. As the materials of the reinforcing wire 24, resin materials, such as polyimide (PI), polyamide imide (PAI), and polyethylene terephthalate (PET) of which the shear strength is higher than that of the inner layer 22 and the first outer layer 34, can be used, in addition to metallic materials, such as tungsten (W), stainless steel (SUS), nickel-titanium-based alloy, steel, titanium, copper, titanium alloys, and copper alloys. In the present embodiment, the reinforcing wire 24 includes thin wires of stainless steel.

The wire reinforcing layer 26 is formed by coiling the reinforcing wire 24 or braiding the reinforcing wire in the shape of a mesh. The number of strands of the reinforcing wire 24, a coil pitch, and the number of meshes are not particularly limited. The wire reinforcing layer 26 of the present embodiment is a braided layer in which the reinforcing wire 24 having a number of strands is braided in the shape of a mesh.

The sub-tubes 28 are hollow tubular members that demarcate the sub-lumens 32. The sub-tubes 28 are buried inside the first outer layer 34. The sub-tubes 28 can be made of, for example, thermoplastic polymer materials. The thermoplastic polymer materials include low-friction resin materials, such as polytetrafluoroethylene (PTFE), polyetheretherketone (PEEK), and tetratluoroethylene-hexafluoropropylene copolymer (FEP). The sub-tubes 28 are made of materials having higher bending rigidity and Young's modulus than the outer layer 38.

As illustrated in FIG. 1, two sub-tubes 28 are arranged around the wire reinforcing layer 26 so as to face each other at 180 degrees, and manipulation wires 30 (30a, 30b) are respectively inserted through the two sub-tubes 28. The two sub-tubes 28 are arranged so as to become parallel to the direction of an axial center of the tubular main body 10.

As illustrated in FIG. 1, the two sub-tubes 28 are arranged on the same circumference so as to surround the main lumen 20. Instead of the present embodiment, three or four sub-tubes 28 may be arranged at equal intervals around the main lumen 20. In this case, the manipulation wires 30 may be arranged in all the sub-tubes 28, or the manipulation wires 30 may be arranged in some sub-tubes 28.

The manipulation wires 30 are slidably and loosely fitted into the sub-tubes 28. Tips of the manipulation wires 30 are fixed to the distal part DE of the tubular main body 10. Since pulling force is applied to positions that are eccentric from the axial center of the tubular main body 10 by pulling the manipulation wires 30 to the base end side, the tubular main body 10 is bent. Since the manipulation wires 30 of the present embodiment are very thin and have high flexibility, no pushing force is substantially applied to the distal part DE of the tubular main body 10 even when the manipulation wires 30 are pushed to a distal side.

Although the manipulation wires 30 may be constituted of a single wire rod, the manipulation wires may be a stranded wire configured by twisting together a plurality of thin wires. Although the number of thin wires that constitutes one stranded wire of the manipulation wires 30 is not particular limited, the number of thin wires is preferably three or more. A suitable example of the number of thin wires is seven or three.

As the manipulation wires 30, metal wires, such as low-carbon steel (music wires), stainless steel (SUS), steel wires coated with corrosion-resistant materials, titanium, titanium alloys, or tungsten, can be used. In addition, as the manipulation wires 30, polyvinylidene fluoride (PVDF), high-density polyethylene (HDPE), poly(para-phenylene benzobisoxazole) (PBO), polyetheretherketone (PEEK), polyphenylene sulfide (PPS), polybutylene terephthalate (PBT), polyimide (PI), polytetrafluoroethylene (PTFE), and polymer fibers, such as boron fibers, can be used.

In the catheter 100 of the present embodiment, the two manipulation wires 30 are inserted through the sub-tubes 28, and are individually fixed to the distal part DE of the tubular main body 10. Here, the manipulation wires 30 being two means that two wires may be individually formed, or one wire may be folded at the distal part DE of the tubular main body 10 or both ends thereof may be individually pulled by the bending manipulation part 60. That is, in the present embodiment, the manipulation wires being two or more means that paths along which the pulling force that bend the distal part DE of the tubular main body 10 are two or more.

The second reinforcing layer 40 is a protective layer that is provided closer to the outer peripheral side than the manipulation wires 30 in the tubular main body 10 to protect the second outer layer 36. As the second reinforcing layer 40 is present on the outer peripheral side of the manipulation wires 30, a situation is prevented in which the manipulation wires 30 break the second outer layer 36 and the hydrophilic layer (not illustrated) and are exposed to the outside of the tubular main body 10.

The second reinforcing layer 40 is formed by coiling the second reinforcing wire 42 or braiding the second reinforcing wire in the shape of a mesh. The above materials exemplified as the reinforcing wire 24 of the wire reinforcing layer 26 can be used for the second reinforcing wire 42. The second reinforcing wire 42 and the reinforcing wire 24 are made of the same kind of resin materials or different kinds of resin materials. In the present embodiment, a braided layer in which a thin wire made of the same kind of materials (stainless steel) as the reinforcing wire 24 is braided in the shape of a mesh is exemplified as the second reinforcing wire 42.

The wire diameters and numbers of strands of the second reinforcing wire 42 and the reinforcing wire 24 may be the same or may be different from each other.

The distal part DE of the tubular main body 10 is provided with a first marker 14 and a second marker 16 located closer to the proximal side than the first marker 14. The first marker 14 and the second marker 16 are ring-shaped members made of materials, such as platinum, through which radiation, such as X-rays, is not transmitted. By using the positions of the two markers including the first marker 14 and the second marker 16 as indexes, the position of the tip of the tubular main body 10 in a body cavity (blood vessel) can be viewed under the observation of the radiation (X-rays). Accordingly, an optimum timing for performing the bending manipulation of the catheter 100 can be easily determined.

The tips of the manipulation wires 30 are fixed to the portion of the tubular main body 10 closer to the distal side than the second marker 16. By pulling the manipulation wires 30, the portion of the distal part DE closer to the distal side than the second marker 16 is bent. In the catheter 100 of the present embodiment, the tips of the manipulation wires 30 are fixed to the first marker 14. The manipulation wires 30 being fixed to the first marker 14 are not particularly limited and can include a solder joint, thermal fusion, adhesion using an adhesive, mechanical latching between the manipulation wires 30 and the first marker 14, and the like.

Proximal ends of the wire reinforcing layer 26 and the second reinforcing layer 40 are located at a proximal end of the tubular main body 10, that is, inside the manipulation part 50.

A distal end of the inner layer 22 may reach the distal end of the tubular main body 10, or may be terminated slightly closer to the base end side than the distal end. The proximal end of the inner layer 22 is located at a proximal end of the tubular main body 10, that is, inside the manipulation part 50.

Here, the typical dimensions of the tubular main body 10 will be described.

The diameter of the main lumen 20 can be 400 µm to 600 µm (including an upper limit and a lower limit; the same applies below), the thickness of the inner layer 22 is 5 µm to 30 µm, and the thickness of the outer layer 38 is 10 µm to 200 µm. The thickness of the sub-tubes 28 are smaller than that of the inner layer 22, and are 1 µm to 10 µm. The internal diameter of the wire reinforcing layer 26 is 410 µm to 660 µm, the external diameter of the wire reinforcing layer 26 is 450 µM to 740 µm, the internal diameter of the second reinforcing layer 40 is 560 µm to 920 µm, and the external diameter of the second reinforcing layer 40 is 600 µm to 940 µm.

The internal diameter of the first marker 14 is 450 µm to 740 µm, the external diameter of the first marker 14 is 490 µm to 820 µm, the internal diameter of the second marker 16 is 600 µm to 940 µm, and the external diameter of the second marker 16 is 640 µm to 960 µm.

The radius (distance) from the axial center of the catheter 100 to the centers of the sub-tubes 28 is 300 µm to 450 µm, the internal diameter (diameter) of the sub-tubes 28 is 40 µm to 100 µm, and the thickness of the manipulation wires 30 is 25 µm to 60 µm.

The diameter of the tubular main body 10 is 700 µm to 980 µm, that is, the external diameter is less than 1 mm, and the tubular main body 10 constitutes a micro catheter capable of being inserted into a peripheral blood vessel.

The coefficient of linear expansion of the tubular main body 10 is greater than the coefficient of linear expansion of the manipulation wires 30. As an example, the coefficient of linear expansion of the tubular main body 10 is 100 ppm/K or more and 300 ppm/K or less, and the coefficient of linear expansion of the manipulation wires 30 is 10 ppm/K or more and 30 ppm/K or less.

Additionally, the swelling coefficient of the tubular main body 10 is greater than the swelling coefficient of the manipulation wires 30. Here, the coefficient of linear expansion or the swelling coefficient of the tubular main body 10 is a coefficient of linear expansion or a swelling coefficient as seen in the entire stacked structure of the tubular main body 10. That is, the coefficient of linear expansion or the swelling coefficient of the tubular main body is a resultant coefficient of linear expansion or a resultant swelling coefficient as a composite structure of the inner layer 22, the outer layer 38, the wire reinforcing layer 26, the second reinforcing layer 40, the sub-tubes 28, and other constituent elements (excluding the manipulation wires 30) that are brought in close contact with each other and integrated with each other. The coefficient of linear expansion or the swelling coefficient of the tubular main body can be estimated by multiplying the independent coefficients of linear expansion or the independent coefficients of expansion or swelling coefficients of the above constituent elements by Young's moduli and area ratios in cross-sectional areas.

In the catheter 100 of the present embodiment, the coefficient of linear expansion and the swelling coefficient of the tubular main body 10 are greater than that of the manipulation wires 30. Therefore, as described above, over-tension can be loaded to the manipulation wires 30 under various environments after the assembly or the packaging of catheters, such as at the time of heating and sterilization or transportation environments in summer. In contrast, in the catheter 100 of the present embodiment, the over-tension can be solved by the operation of the manipulation part 50. Hereinafter, the structure and the operation of the manipulation part 50 of the present embodiment will be described in detail with reference to FIGS. 4 to 13.

Figure 4:
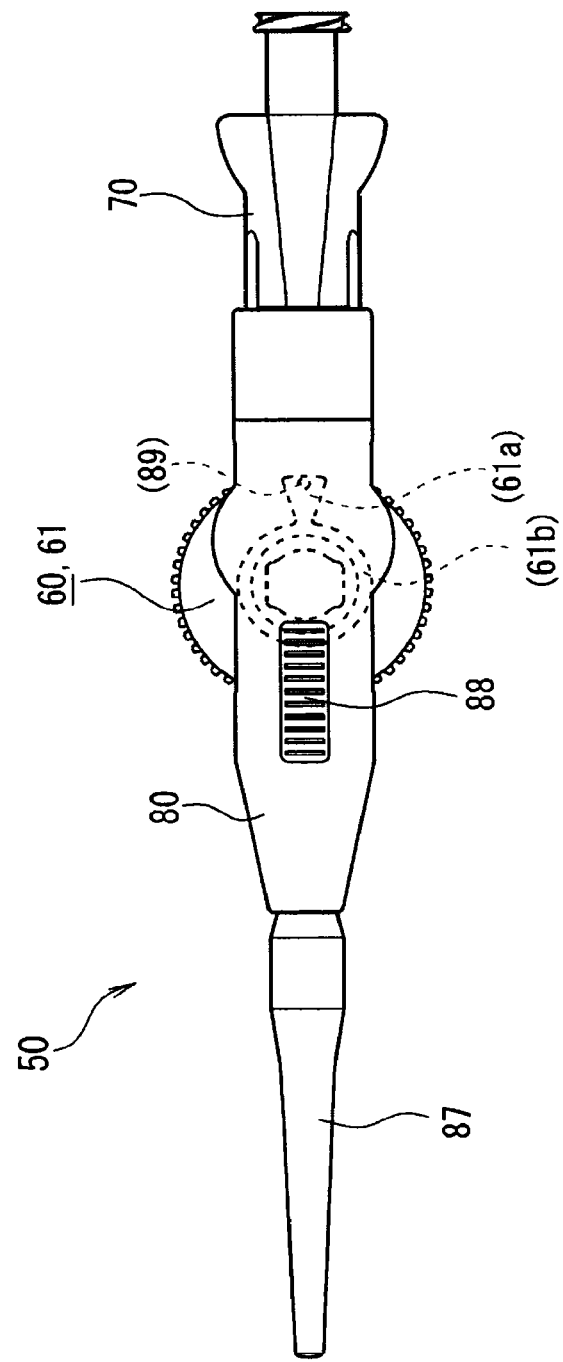
FIG. 4 is a plan view of a catheter manipulation part when the bending manipulation part is at a retracted position.
Figure 5:
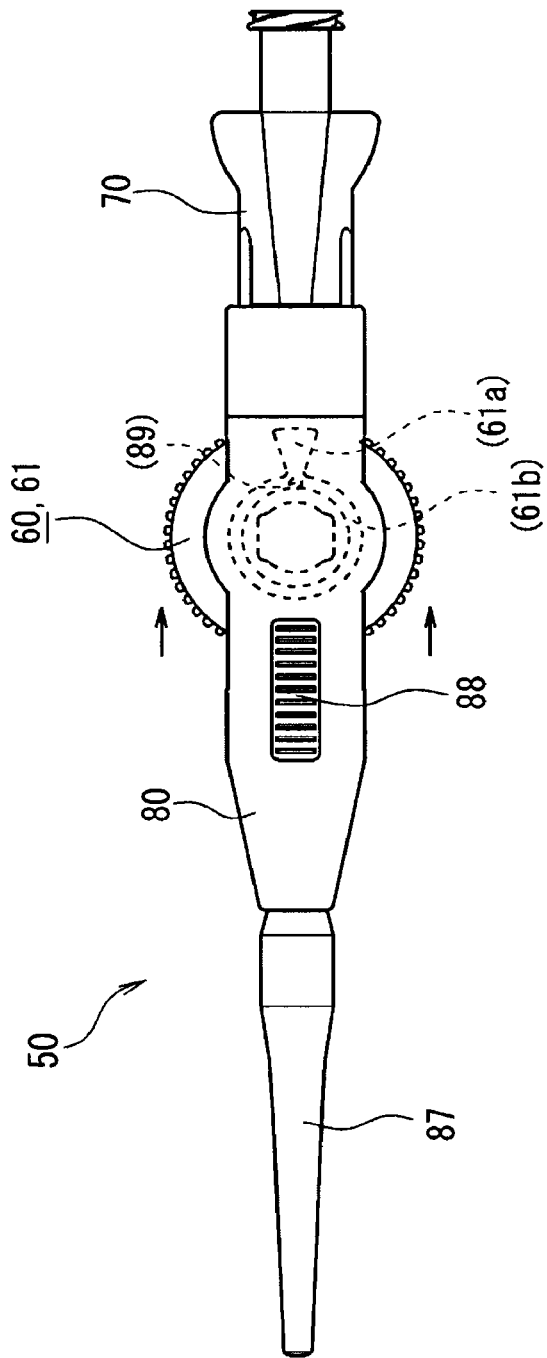
FIG. 5 is a plan view of the catheter manipulation part when the bending manipulation part is at a manipulation position.
Figure 6:
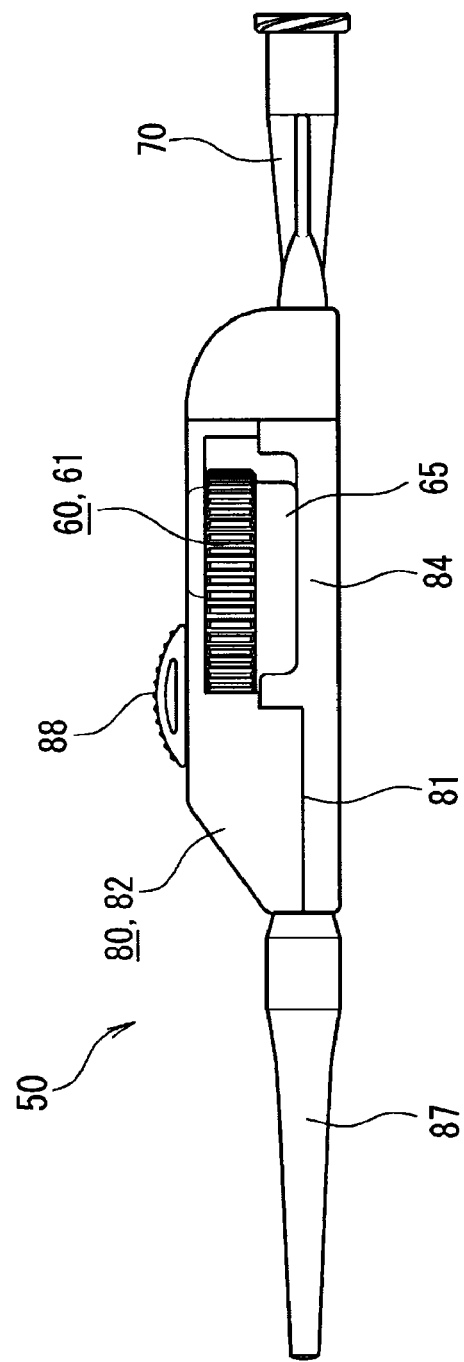
FIG. 6 is a side view of the catheter manipulation part when the bending manipulation part is at the retracted position.
Figure 7:
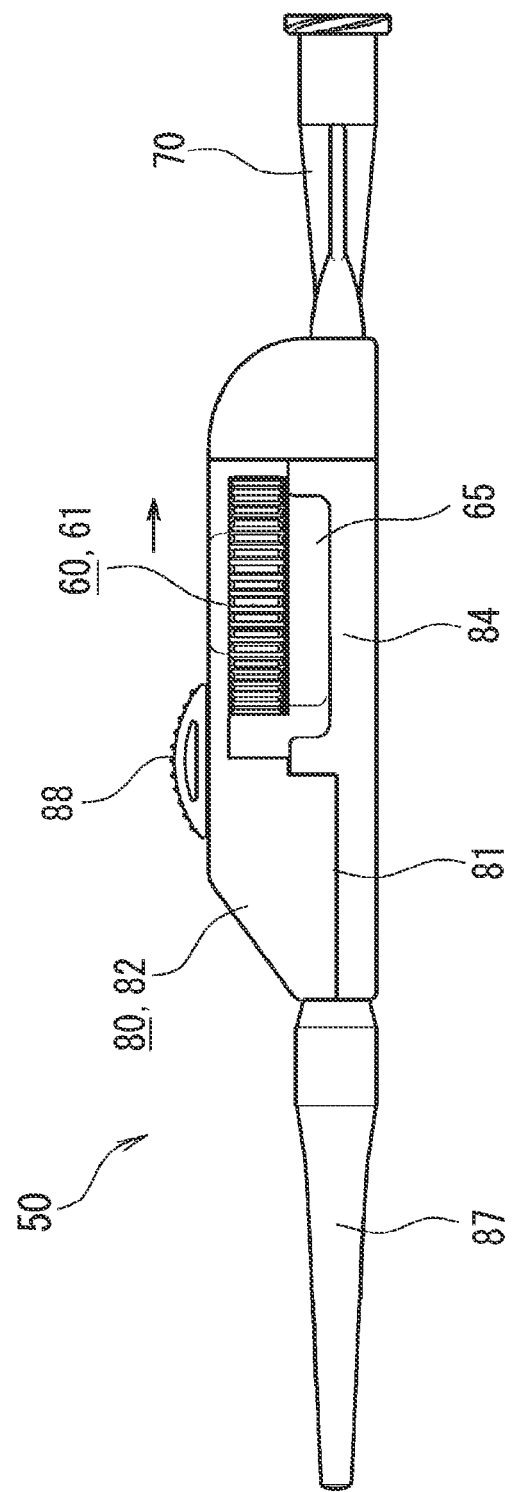
FIG. 7 is a side view of the catheter manipulation part when the bending manipulation part is at the manipulation position.
Figure 8:
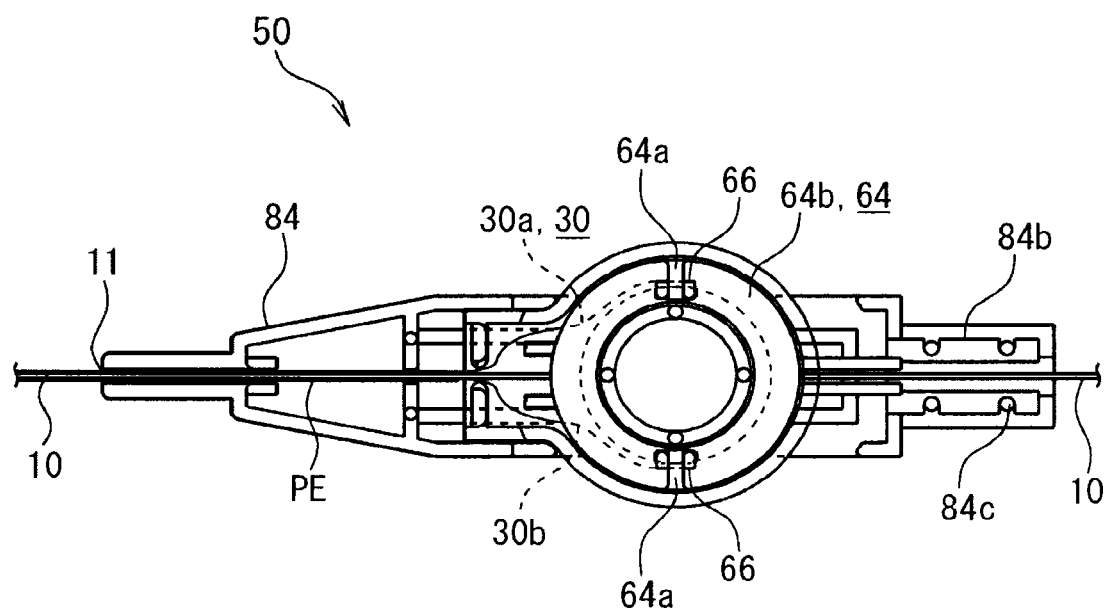
FIG. 8 is a plan view illustrating the state of manipulation wires when the bending manipulation part is at the retracted position.

FIGS. 4 and 5 are plan views of the manipulation part 50, and FIGS. 6 and 7 are side views of the manipulation part 50. FIGS. 8 and 9 are plan views describing the state of the manipulation wires 30, and illustrate the internal structure of the manipulation part 50.

FIGS. 4, 6, and 8 illustrate the manipulation part 50 in a state (hereinafter referred to as a retracted state) where the bending manipulation part 60 is at a retracted position.

FIGS. 5, 7, and 9 illustrate the manipulation part 50 in a state (hereinafter referred to as a manipulated state) where the bending manipulation part 60 is at a manipulation position.

Figure 10:
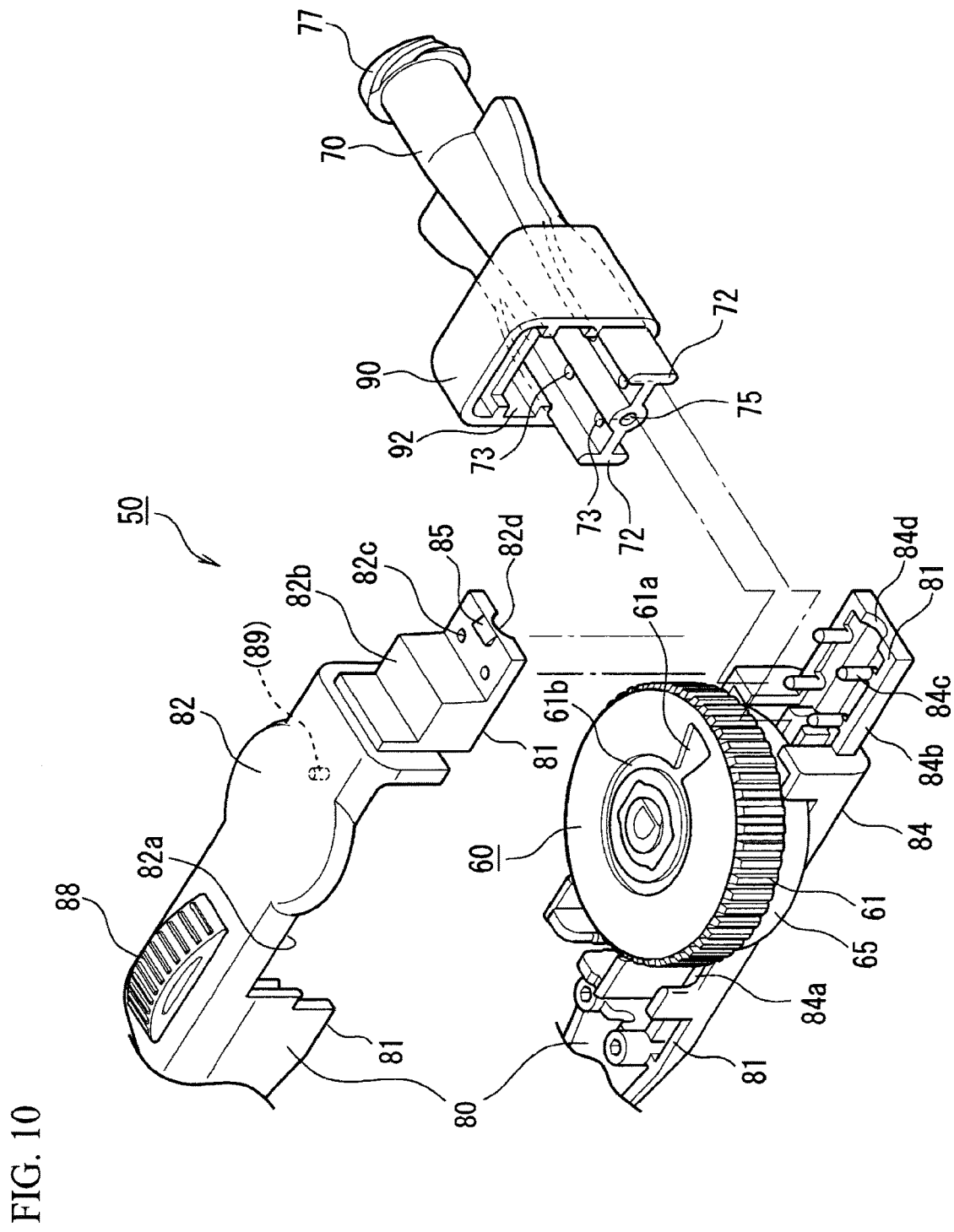
FIG. 10 is an exploded perspective view of the catheter manipulation part.
Figure 11:
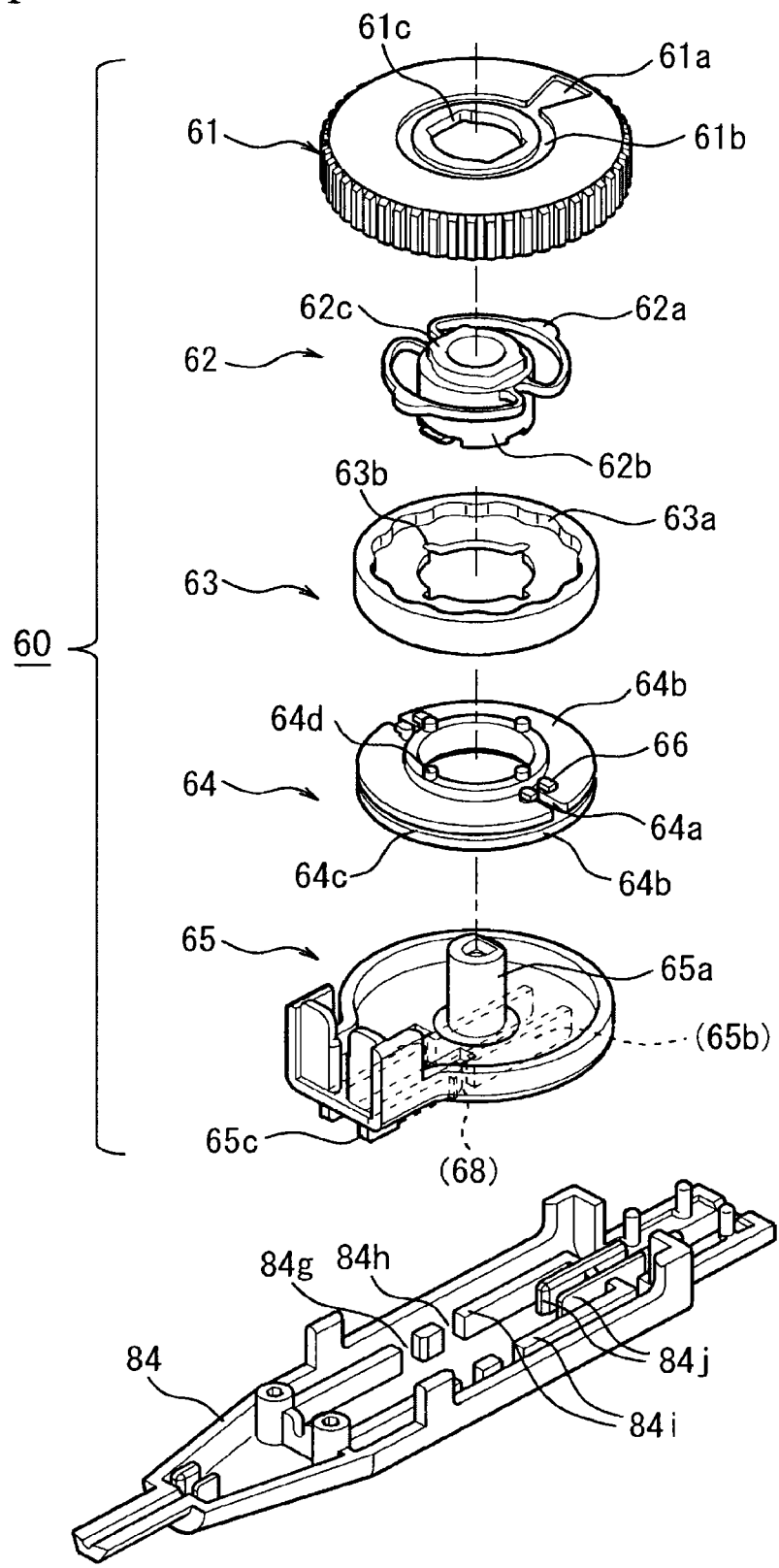
FIG. 11 is an exploded side view of a manipulation-part main body and the bending manipulation part.

FIG. 10 is an exploded perspective view of the manipulation part 50, and FIG. 11 is an exploded side view of the manipulation-part main body 80 and the bending manipulation part 60.

In the following description, the arrangement side of the upper main body 82 in the manipulation-part main body 80 may be referred to as an upper side and the arrangement side of the lower main body 84 may be referred to as a lower side. However, this is for describing the relative positions of members in the catheter 100 for convenience. The upper side and the lower side do not mean up and down in the gravitational direction when the catheter 100 is manufactured or used.

The length of the manipulation part 50, that is, the length from the tip of the protector 87 to the rear end of the hub connector 70, is about 5 cm to about 15 cm.

As illustrated in FIGS. 4 and 5, the manipulation part 50 has a pulling restricting part 89. The pulling restricting part 89 restricts that the bending manipulation part 60 at the retracted position illustrated in FIGS. 4, 6, and 8 applies pulling force to the manipulation wires 30 (refer to FIG. 8). Here, aspects in which the pulling restricting part 89 restricts that the bending manipulation part 60 applies the pulling force to the manipulation wires 30 includes an aspect in which the pulling restricting part 89 restricts the operation of the bending manipulation part 60 and an aspect in which application of the pulling force to the manipulation wires 30 is suppressed even when the bending manipulation part 60 is operated.

In the present embodiment, an aspect in which the pulling restricting part 89 restricts the operation of the bending manipulation part 60 is exemplified. The pulling restricting part 89 of the present embodiment is latched to the bending manipulation part 60 to restrict pulling manipulations. Specifically, as illustrated in FIG. 4, the pulling restricting part 89 is fitted to an extending recess 61a formed in an upper surface of the dial manipulation part 61 of the bending manipulation part 60.

As illustrated in FIGS. 10 and 11, an annular groove 61b is formed by shaving off the upper surface of the dial manipulation part 61 coaxially on the rotational axis of the dial manipulation part 61. The extending recess 61a and the annular groove 61b are continuously formed. The extending recess 61a extends outward in the radial direction of the dial manipulation part 61 from a portion of the periphery of the annular groove 61b. The extending recess 61a is a tapered recess of which the width decreases toward the annular groove 61b. The extending recess 61a forms a fan shape in a plan view. Although the central angle of the fan-shaped extending recess 61a is not particularly limited, 90 degrees or less is preferable.

As illustrated in FIGS. 4 and 10, the dial manipulation part 61 is mounted on the manipulation-part main body 80 such that the annular groove 61b is directed to a rear end side corresponding to a mounting side of the hub connector 70 in an initial state.

In the manipulation part 50 in the retracted state, the pulling restricting part 89 engages with a substantially central part or a tip side (an outer peripheral side in the dial manipulation part 61) of the extending recess 61a. Since the extending recess 61a has the fan-shaped tapered shape, the dial manipulation part 61 in the retracted state can be rotated by an angle equivalent to the central angle of the fan-shaped extending recess 61a. That is, some "play", that is, a minute rotatable angle, (free play angle) is present in the dial manipulation part 61 in the retracted state. The central angle of the extending recess 61a can be 90 degrees or less, and preferably 60 degrees or less in order to prevent that the free play angle becomes excessive and an unexpected pulling force is applied to the manipulation wires 30.

A situation in which the pulling restricting part 89 restricts that the bending manipulation part 60 applies slight pulling force to the manipulation wires 30 in the retracted state of the manipulation part 50 does not exclude a situation in which such a free play angle is present and the bending manipulation part 60 applies pulling force to the manipulation wires 30 within this angle range.

Then, as the bending manipulation part 60 transits to the manipulation position illustrated in FIGS. 5 and 7 from the retracted position illustrated in FIGS. 4 and 6, the restriction of the pulling restricting part 89 is released. Specifically, as the bending manipulation part 60 moves in a transition direction indicated by arrows in FIGS. 5 and 7, the pulling restricting part 89 that has engage with the extending recess 61a relatively moves from the extending recess 61a to the annular groove 61b. Accordingly, the pulling restricting part 89 becomes relatively rotatable around the dial manipulation part 61 along the annular groove 61b.

When the manipulation part 50 is in the manipulated state, the bending manipulation part 60 may rotate freely without angle restrictions with respect to the manipulation-part main body 80, or the rotatable angle may be specified to a predetermined angle of less than 360 degrees. In this case, the rotatable angle of the bending manipulation part 60 in the manipulated state is greater than the central angle of the extending recess 61a corresponding to the free play angle of the bending manipulation part 60 in the retracted state. The rotatable angle can be, for example, 270 degrees or more and less than 360 degrees, that is, 135 degrees or more and less than 180 degrees in normal and reverse directions from the initial state of FIG. 4.

The lock slider 88 may engage with the bending manipulation part 60 at the retracted position to restrict the rotation of the bending manipulation part 60, or may not engage with the bending manipulation part 60. This is because the rotatable angle of the bending manipulation part 60 at the retracted position is restricted to a small value by the extending recess 61a.

Meanwhile, the lock slider 88 slides so as to be capable of being brought close to and separated from the bending manipulation part 60 at the manipulation position, and engages with the dial manipulation part 61. This restricts the rotation of the bending manipulation part 60, as illustrated in FIGS. 1(b) and 1(c).

The bending manipulation part 60 of the present embodiment can transit to the manipulation position and the retracted position with respect to the manipulation-part main body 80. The transition direction of the bending manipulation part 60 from the retracted position to the manipulation position is the direction of a tip and a base end of the manipulation-part main body 80, and is the direction of the axial center of the tubular main body 10. As illustrated in FIGS. 6 and 7, the manipulation-part main body 80 sandwiches the bending manipulation part 60 from the vertical direction with the upper main body 82 and the lower main body 84. A separation surface 81 corresponding to an interface between the upper main body 82 and the lower main body 84 is parallel to the transition direction of the bending manipulation part 60. More specifically, the retracted position of the bending manipulation part 60 is the tip side of the manipulation-part main body 80 on which the protector 87 is mounted, and the transition position is the rear end side of the manipulation-part main body 80 on which the hub connector 70 is mounted.

FIG. 8 is a plan view illustrating the internal structure of the manipulation part 50 in the retracted state, and FIG. 9 is a plan view illustrating the internal structure of the manipulation part 50 in the manipulated state. In FIGS. 8 and 9, the illustration of the upper main body 82, the lock slider 88, the dial manipulation part 61, the limiter member 62, an engaging member 63 (refer to FIG. 11), the hub connector 70, the protector 87, and a reinforcing member 90 (refer to FIG. 10) is omitted. In FIGS. 8 and 9, that base end PE of the tubular main body 10 introduced into the manipulation-part main body 80 and the manipulation wires 30 (30a, 30b) laterally pulled out of the tubular main body 10 is illustrated.

The base end PE of the tubular main body 10 passes through a lower part of the bending manipulation part 60, and is pulled out up to a position closer to the rear side than a rear end 84b of the manipulation-part main body 80 (lower main body 84). Side holes (not illustrated) ranging from the outer peripheral surface to the sub-tubes 28 are drilled at positions corresponding to the inside of the manipulation-part main body 80, in the base end PE of the tubular main body 10. The side holes pass through the peripheral surfaces of the sub-tubes 28. The manipulation wires 30 are pulled out to the external lateral sides of the sub-tubes 28 through the side holes. The manipulation wires 30 are pulled out of slits 64a and are tied up and fixed to the engagement parts 66 provided in a wire fixing disk 64 after being wound around the wire fixing disk 64.

That is, the bending manipulation part 60 has a plurality of the engagement parts 66, and base ends of the plurality of manipulation wires 30a and 30b engage with the engagement parts 66. As a specific engagement aspect, the manipulation wires 30a and 30b are anchored with an adhesive after being subjected to compounding with respect to the engagement parts 66.

The two manipulation wires 30a and 30b are wound around the wire fixing disk 64 in mutually opposite directions. The manipulation wires 30a and 30b are each wound around the wire fixing disk 64 at a winding angle exceeding 360 degrees. Accordingly, even if the bending manipulation part 60 is rotationally manipulated over 360 degrees from the initial state of FIG. 1(a), the delivery length of a manipulation wire 30 on the loosened side is not insufficient.

As illustrated in FIG. 10, the manipulation part 50 includes the manipulation-part main body 80, the bending manipulation part 60, the hub connector 70, and the reinforcing member 90. The upper main body 82 and the lower main body 84 are half bodies that constitute the manipulation-part main body 80. A lower surface of the upper main body 82 and an upper surface of the lower main body 84 are joined to each other to constitute the separation surface 81. The upper main body 82 has an upper recess 82a that opens below. The lower main body 84 has a lower recess 84a that opens upward. By combining the upper main body 82 and the lower main body 84, the upper recess 82a and the lower recess 84a constitute a mounting space for the bending manipulation part 60.

An insertion protrusion 82b is formed on a rear part of the upper main body 82 so as to protrude therefrom. A plurality of pin holes 82c are drilled in the insertion protrusion 82b, and a claw-like engagement part 85 is formed at a rear end of the insertion protrusion. The insertion protrusion 82b is inserted into an opening 92 of the reinforcing member 90.

A plurality of pins 84c that protrude upward are formed on an upper surface of the rear end 84b extending to a rear part of the lower main body 84. A plurality of pin holes 73 passing through a front end of the hub connector 70 in its thickness direction are drilled in the front end. By combining the upper main body 82 and the lower main body 84, the plurality of pins 84c passes through the pin holes 73 of the hub connector 70, and are inserted into the pin holes 82c. This prevents the hub connector 70 from dropping out of the manipulation-part main body 80 consisting of the upper main body 82 and the lower main body 84.

A rear end of the hub connector 70 is provided with a mounting port 77 for mounting a syringe in a threadedly engaged manner. The syringe is mounted on the mounting port 77. A front end of the hub connector 70 is provided with a tip opening 75 communicating with the mounting port 77. Reinforcing ribs 72 are erected from the hub connector 70 on both sides in the width direction with the tip opening 75 being interposed therebetween. The reinforcing ribs 72 prevent crushing of the tip opening 75.

The reinforcing member 90 is an annular member that restricts the separation between the upper main body 82 and the lower main body 84, and reinforces an attachment between the manipulation-part main body 80 and the hub connector 70. In a state where the hub connector 70 is sandwiched by the upper main body 82 and the lower main body 84, spacing-apart of the separation surface 81 between the upper main body 82 and the lower main body 84 is prevented by mounting the reinforcing member 90 around the insertion protrusion 82b and the rear end 84b.

Half-split cylindrical recessed grooves 82d and 84d are respectively formed on an upper surface side of the lower recess 84a and on a lower surface side of the upper recess 82a. By combining the upper main body 82 and the lower main body 84, the recessed grooves 82d and 84d are put together to constitute a columnar gap. The base end PE of the tubular main body 10 is mounted on this gap part (refer to FIGS. 8 and 9).

The engagement part 85 of the manipulation-part main body 80 (upper main body 82) is locked to the reinforcing member 90. This prevents the reinforcing member 90 mounted around the insertion protrusion 82b and the rear end 84b of the manipulation-part main body 80 from dropping out of the manipulation-part main body 80.

As illustrated in FIG. 11, the bending manipulation part 60 of the present embodiment includes the dial manipulation part 61, the limiter member 62, the engaging member 63, the wire fixing disk 64, and a shaft member 65.

The dial manipulation part 61 is a rotary board that is arranged on the outer peripheral side of the bending manipulation part 60 and is manipulated by an operator directly coming into contact with the rotary board with his/her fingers. The extending recess 61a and the annular groove 61b are formed as described above on the upper surface side of the dial manipulation part 61. A non-circular opening 61c is formed at an axial center of the dial manipulation part 61.

The limiter member 62 is non-rotatably mounted on the dial manipulation part 61. The limiter member 62 has a spring engagement part 62a and a shaft part 62b. The spring engagement part 62a is an elastically deformable member that is deformed so as to be extendable and retractable in the radial direction of the limiter member 62. A rotating shaft 65a of the shaft member 65 is inserted through the shaft part 62b. A non-circular locking protrusion 62c is formed in the state of the shaft part 62b. The locking protrusion 62c is non-rotatably fitted to the opening 61c of the dial manipulation part 61. Accordingly, the limiter member 62 and the dial manipulation part 61 are integrated and rotated around the rotating shaft 65a.

The engaging member 63 is an annular member that allows the shaft part 62b of the limiter member 62 to be inserted therethrough and disengageably engage with the spring engagement part 62a. The engaging member 63 has a bottomed annular shape, and has a wave-like irregular part 63a formed in an inner peripheral surface of a circular peripheral wall thereof. The spring engagement part 62a of the limiter member 62 engages with the irregular part 63a in a plurality of places in the circumferential direction thereof. When the limiter member 62 and the engaging member 63 are relatively twisted with a torque equal to or more than a predetermined value, the engagement between the spring engagement part 62a and the irregular part 63a is released. The engaging member 63 has a plurality of recessed cutouts 63b.

The wire fixing disk 64 is a bobbin around which the manipulation wires 30a and 30b are wound (refer to FIGS. 8 and 9). The wire fixing disk 64 includes a pair of larger-diameter flanges 64b, and a smaller-diameter winding part 64c formed between the flanges. One (an upper flange 64b in FIG. 11 in the present embodiment) of the flanges 64b is formed with the slits 64a and the engagement parts 66. As illustrated in FIGS. 8 and 9, the two manipulation wires 30a and 30b laterally pulled out of the base end PE of the tubular main body 10 are pulled out of the slits 64a after being wound around the wire fixing disk 64 in mutually opposite directions and wound 360 degrees or more. The ends of the pulled-out manipulation wires 30a and 30b are bonded and fixed after being tied up to the engagement parts 66.

A plurality of projections 64d are formed on an upper surface of the wire fixing disk 64. As the projections 64d are fitted to the recessed cutouts 63b of the engaging member 63, the engaging member 63 is non-rotatably fixed to the wire fixing disk 64, and both of the engaging member and the wire fixing disk are rotatably journalled to the shaft member 65.

As described above, as the limiter member 62 and the engaging member 63 are mutually twisted with a torque equal to or more than a predetermined value, the engagement between the spring engagement part 62a of the limiter member 62 and the engaging member 63 is released. For this reason, when a user has applied the above torque equal to or more than a predetermined value to the dial manipulation part 61, this torque is not transmitted to the manipulation wire 30a or 30b through the engaging member 63 and the wire fixing disk 64. In other words, the limiter member 62 and the engaging member 63 constitute a tension limiter that prevents breaking of the manipulation wires 30a and 30b.

The shaft member 65 is a holding member having a circular recess that houses the wire fixing disk 64 and is slidable with respect to the lower main body 84. The shaft member 65 includes the rotating shaft 65a that protrudes upward, and guide ribs 65b and 65c that protrude downward.

The dial manipulation part 61, the limiter member 62, the engaging member 63, and the wire fixing disk 64 are rotatably mounted on the rotating shaft 65a. Accordingly, the bending manipulation part 60 is integrally configured.

The guide ribs 65b and 65c are two pairs of parallel plate-like projections. A pair of guide ribs 65c are formed with claws (transition restricting parts 68) that protrude outward. The transition restricting parts 68 are elastically deformed so as to be extendable and retractable in the width direction of the lower main body 84. The transition restricting parts 68 form an arrowhead shape that has a front end side (the left of FIGS. 12 and 13) as a folded part.

The lower main body 84 includes inner guides 84j that slides in contact with the guide ribs 65b, and intermittent ribs 84i that slide in contact with the guide ribs 65c. The inner guides 84j and the intermittent ribs 84i are a pair of plate-like protrusions that extend in a forward-backward direction of the lower main body 84. The pair of intermittent ribs 84i are a set of a plurality of rib pieces that are divided by and discretely formed by at least two gaps (a retraction-side gap 84g and a manipulation-side gap 84h).

When the shaft member 65 is mounted on the lower main body 84, the guide ribs 65c are arranged along the inside of the pair of intermittent ribs 84i, and the guide ribs 65b are sandwiched and arranged between the inner guides 84j and the intermittent rib 84i. Accordingly, the bending manipulation part 60 formed by integrally combining the dial manipulation part 61, the limiter member 62, the engaging member 63, the wire fixing disk 64, and the shaft member 65 is attached so as to be slidable in the forward-backward direction of the lower main body 84.

Figure 12:
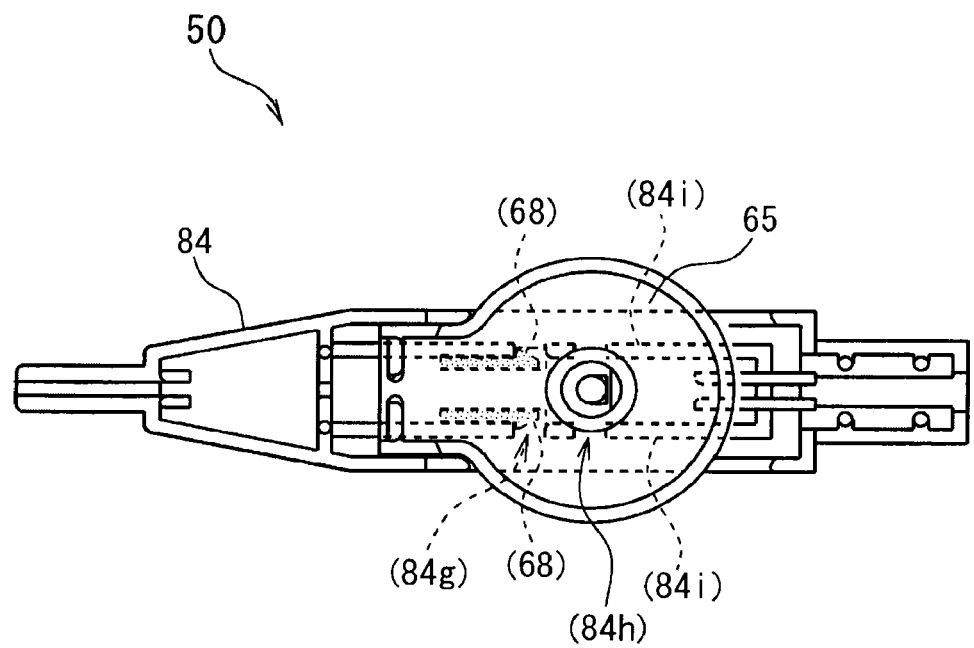
FIG. 12 is a plan view illustrating a positional relationship between the bending manipulation part at the retracted position and the manipulation-part main body.
Figure 13:
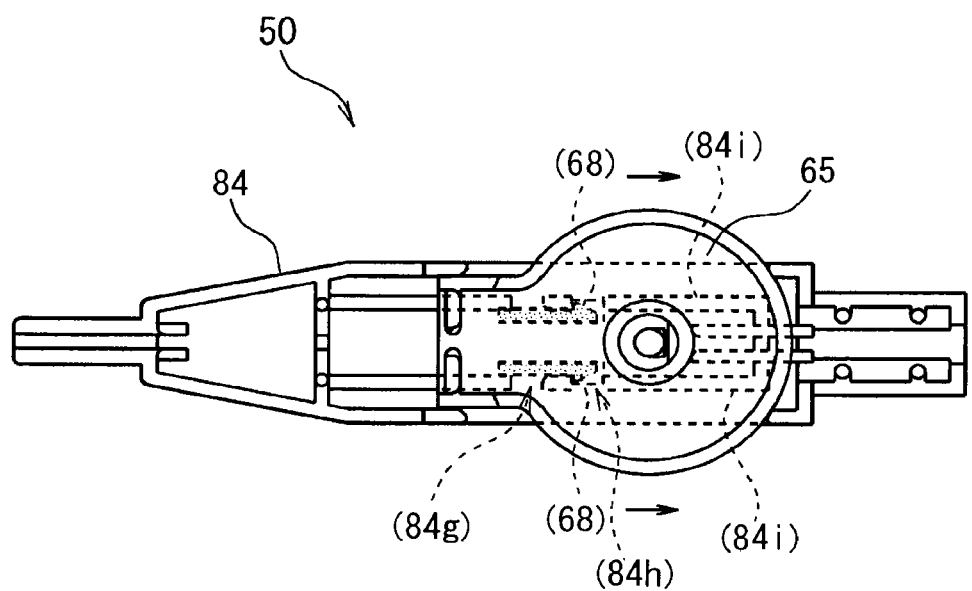
FIG. 13 is a plan view illustrating a positional relationship between the bending manipulation part at the manipulation position and the manipulation-part main body.

FIGS. 12 and 13 are plan views illustrating a positional relationship between the bending manipulation part 60 (shaft member 65) and the manipulation-part main body 80 (lower main body 84).

In the retracted state illustrated in FIG. 12, the transition restricting parts 68 engage with the retraction-side gaps 84g corresponding to gaps on front end sides in the intermittent ribs 84i. When the bending manipulation part 60 (shaft member 65) transits to the manipulated state illustrated in FIG. 13, the transition restricting parts 68 engage with the manipulation-side gaps 84h corresponding to gaps the rear end sides in the intermittent ribs 84i. Since the transition restricting parts 68 forms an arrowhead shape as described above, as the transition restricting parts engage with the gaps of the intermittent ribs 84i, the movement from the front end side of the lower main body 84 to the rear end side thereof (from the left of FIGS. 12 and 13 to the right) is allowed, and the movement from the rear end side of the lower main body to the front end side thereof (from the right of FIGS. 12 and 13 to the left) is restricted.

That is, the manipulation part 50 of the present embodiment has the transition restricting parts 68, and the transition restricting parts 68 allow the transition of the bending manipulation part 60 from the retracted position to the manipulation position, and restrict the transition of the bending manipulation part 60 from the manipulation position to the retracted position. Then, the plurality of engagement parts 66 of the bending manipulation part 60 move integrally by causing the bending manipulation part 60 to transit from the retracted position to the manipulation position.

The manipulation position and the retracted position of the bending manipulation part 60 are arranged side by side in the axial direction of the tubular main body 10. Here, the axial direction of the tubular main body 10 means an extending direction of the base end PE (refer to FIGS. 8 and 9) of the tubular main body 10 pulled into the manipulation-part main body 80.

As described above, the path lengths of the manipulation wires 30 from the base end PE of the tubular main body 10 to the engagement parts 66, as illustrated in FIG. 9, mean lengths until the manipulation wires 30 that are stretched without loosening the reach the engagement parts 66, from the pull-in position 11 of the tubular main body 10 with respect to the manipulation-part main body 80.

The path lengths of the manipulation wires 30 when the bending manipulation part 60 is at the retracted position are shorter than the path lengths of the manipulation wires 30 when the bending manipulation part 60 is at the manipulation position. For this reason, as illustrated in FIG. 8, when the bending manipulation part 60 is at the retracted position, the manipulation wires 30 are loosened. As illustrated in FIG. 9, when the bending manipulation part 60 transits from the retracted position to the manipulation position, the loosening of the manipulation wires 30 are removed. Then, as the bending manipulation part 60 at the manipulation position performs pulling manipulations, pulling force is applied to the plurality of manipulation wires 30a and 30b, and the distal part DE of the tubular main body 10 is bent.

In this way, when the bending manipulation part 60 of which the rotation has been restricted at the retracted position is made to transit to the manipulation position, the loosening of the manipulation wires 30 is removed, and the bending manipulation part 60 becomes rotatable. Accordingly, by disposing the bending manipulation part 60 at the retracted position in the initial state after the assembly of the catheter 100, heat deformation or swelling deformation can be absorbed by virtue of the loosening of the manipulation wires 30 even if this heat deformation or swelling deformation has occurred in the tubular main body 10 and the manipulation wires 30 and the tubular main body 10 has elongated more greatly than the manipulation wires 30.

That is, it is desirable to dispose the bending manipulation part 60 at the retracted position when the catheter 100 is heated and sterilized and to cause the bending manipulation part 60 to transit from the retracted position to the manipulation position after the heating and the sterilizing. Accordingly, it is possible to remove the loosening of the manipulation wires 30 and perform pulling manipulations using the bending manipulation part 60, and the distal part DE (refer to FIG. 3) of the tubular main body 10 can be appropriately bent and manipulated.

That is, as a method for manufacturing the above catheter 100, it is desirable to perform a step of preparing the catheter 100 in which the bending manipulation part 60 is at the retracted position; a step of housing the catheter 100 in a sterilizing package (not illustrated) to heat and sterilize the catheter; and a step of causing the bending manipulation part 60 in the heated and sterilized catheter 100 to transit from the retracted position to the manipulation position, thereby removing some or all of loosening of the manipulation wires 30*a* and 30*b*.

The step of causing the bending manipulation part 60 to transit from the retracted position to the manipulation position may be performed by moving the bending manipulation part 60 from on the sterilizing package, in a state where the catheter 100 has been housed in the sterilizing package. Otherwise, the above step may be carried out after the catheter 100 is taken out from the sterilizing package.

Although an aspect in which the pulling restricting part 89 restricts the operation of the bending manipulation part 60 has been described in the above embodiment, an aspect in which application of the pulling force to the manipulation wires 30 is suppressed even if the bending manipulation part 60 operates may be adopted instead of the present embodiment. Specifically, the bending manipulation part 60 and the manipulation wires 30 may be detachably configured in the engagement parts 66. The bending manipulation part 60 and the manipulation wires 30 may be disengaged from each other in the engagement parts 66 in the retracted state of the bending manipulation part 60, and the bending manipulation part 60 and the manipulation wires 30 may engage with each other in the engagement parts 66 in the manipulated state of the bending manipulation part 60. Accordingly, it is possible to suppress a situation in which the bending manipulation part 60 rotates freely in the retracted state and the manipulated state and pulling force are applied to the manipulation wires 30 in the retracted state.

Second Embodiment

Figure 14:
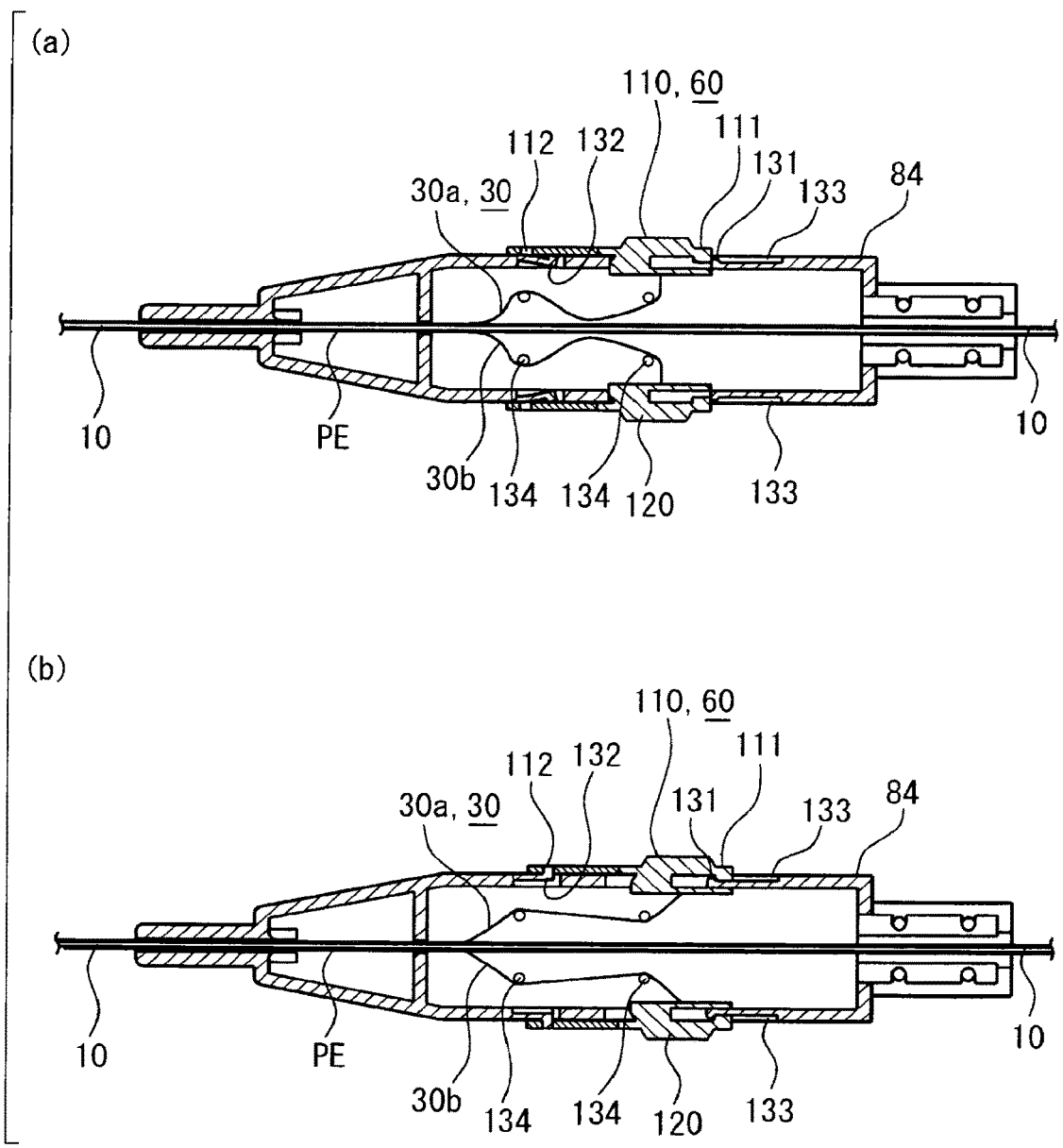
FIG. 14 are longitudinal sectional views illustrating the internal structure of the catheter manipulation part of a second embodiment of the invention.

FIGS. 14(*a*) and 14(*b*) are longitudinal sectional views illustrating the internal structure of the manipulation part 50 of a second embodiment of the invention. FIG. 14(*a*) illustrates a retracted state, and FIG. 14(*b*) illustrates a manipulated state. The illustration of the reinforcing member 90 and the hub connector 70 are omitted.

The manipulation part 50 of the present embodiment is different from the first embodiment in that the bending manipulation part 60 has a plurality of sliding parts 110 and 120 that individually move forward and backward with respect to the manipulation-part main body 80.

The base ends of the plurality of manipulation wires 30*a* and 30*b* engage with the sliding parts 110 and 120, respectively. Then, the plurality of sliding parts 110 and 120 are integrally moved by causing the bending manipulation part 60 to transit from the retracted position to the manipulation position.

The sliding parts 110 and 120 are individually provided to face the manipulation-part main body 80 (lower main body 84). The sliding parts 110 and 120 have engaging protrusions 111 formed on rear end sides (right sides of FIG. 14) of sliding main bodies thereof. Sliding rings 112 having locking holes are mounted on front end sides (left sides of FIG. 14) of the sliding parts 110 and 120.

An outer peripheral surface of the manipulation-part main body 80 (lower main body 84) is formed with a claw 131 and a sliding groove 133 formed continuously with the claw 131. Additionally, the lower main body 84 includes locking pieces 132 on the front end sides of the sliding parts 110 and 120. The locking pieces 132 are elastically deformed so as to be extendable and retractable laterally from the lower main body 84 (vertical direction in each of FIG. 14). The locking pieces 132 do not engage with the locking holes of the sliding rings 112 in the retracted state illustrated in FIG. 14(*a*).

The manipulation wires 30 are pulled out of the base end PE of the tubular main body 10, are drawn around inside the lower main body 84, and are connected to the sliding parts 110 and 120. One or a plurality of sliding projections 134 are formed on the paths of the manipulation wires 30. The sliding projections 134 specify the paths of the manipulation wires 30 that are drawn around inside the manipulation-part main body 80 (lower main body 84).

In the retracted state illustrated in FIG. 14(*a*), the manipulation wires 30 are loosened inside the lower main body 84. In this state, the engaging protrusions 111 of the sliding parts 110 and 120 do not engage with the claw 131, and sliding manipulation of the sliding parts 110 and 120 is restricted. That is, the claw 131 is equivalent to the pulling restricting part 89 of the first embodiment that restricts that the bending manipulation part 60 (sliding parts 110 and 120) at the retracted position applies pulling force to the manipulation wires 30.

By causing the sliding rings 112 to slide to the rear end side from this retracted state, the sliding parts 110 and 120 integrally moves in the same direction and transits to the manipulated state illustrated in FIG. 14(*b*). Accordingly, since the path lengths of the manipulation wires 30 are increased, the loosening of the manipulation wires 30 is removed. Additionally, in the state of the manipulation illustrated in FIG. 14(*b*), the locking pieces 132 engage with the locking holes of the sliding rings 112. Accordingly, the sliding of the sliding rings 112 is restricted, and the sliding parts 110 and 120 are prohibited from returning to the retracted state from the manipulated state. That is, the locking pieces 132 function as the transition restricting part 68 that restricts the transition of the bending manipulation part 60 (sliding parts 110 and 120) from the manipulation position to the retracted position.

When the bending manipulation part 60 (sliding parts 110 and 120) transits from the retracted position to the manipulation position, the pulling restriction using the pulling restricting part 89 (claw 131) is released. Specifically, the engaging protrusions 111 engage with the claw 131 in the manipulated state. Accordingly, the engaging protrusions 111 become slidable to the rear end side along the sliding groove 133. Therefore, by causing the sliding parts 110 and 120 to slide individually with respect to the sliding groove 133, the manipulation wires 30*a* and 30*b* are pulled, respectively, and the distal part DE (refer to FIG. 3) of the tubular main body 10 is bent.

In addition, the various constituent elements of the invention do not need to be individually and independently present, and the invention allows that a plurality of constituent elements are formed as one member, one constituent element is formed by a plurality of members, that a certain constituent element is a portion of another constituent element, that a portion of a certain constituent element and a portion of another constituent element overlap each other, or the like.

The present embodiment include the following technical ideas.

(1) A catheter comprising: an elongated flexible tubular main body; a plurality of manipulation wires inserted through the tubular main body and having tips connected to a distal part of the tubular main body; a manipulation-part main body provided at a base end of the tubular main body; and a bending manipulation part having an engagement part engaging with base ends of the manipulation wires, and individually applying pulling force to the plurality of manipulation wires through pulling operations so as to bend the distal part of the tubular main body, wherein the bending manipulation part is provided so as to be movable with respect to the manipulation-part main body, and wherein the path lengths of the plurality of manipulation wires from the tips thereof to the engagement part are simultaneously increased or decreased when the bending manipulation part and the manipulation-part main body move relative to each other.

(2) The catheter according to the above (1), wherein the bending manipulation part is capable of transiting to a manipulation position or a retracted position with respect to the manipulation-part main body, wherein the path lengths when the bending manipulation part is at the retracted position are shorter than the path lengths when the bending manipulation part is at the manipulation position, and wherein when the bending manipulation part at the manipulation position performs pulling manipulations, the pulling force is applied to the plurality of manipulation wires and the distal part of the tubular main body is bent.

(3) The catheter according to the above (2), wherein the manipulation position and the retracted position are arranged side by side in an axial direction of the tubular main body.

(4) The catheter according to the above (2) or (3), wherein the bending manipulation part includes a plurality of the engagement parts, and the base ends of the plurality of manipulation wires respectively engage with the engagement parts, and wherein the plurality of engagement parts are integrally moved when the bending manipulation part transits from the retracted position to the manipulation position.

(5) The catheter according to any one of the above (2) to (4), wherein the bending manipulation part is rotatable with respect to the manipulation-part main body, and wherein a first manipulation wire of the manipulation wires is tensioned and a second manipulation wire of the manipulation wires is loosened when the bending manipulation part is rotated in one direction, and the second manipulation wire is tensioned and the first manipulation wire is loosened when the bending manipulation part is rotated in the other direction.

(6) The catheter according to the above (2) or (3), wherein the bending manipulation part includes a plurality of sliding parts that individually moves forward and backward with respect to the manipulation-part main body, wherein the base ends of the plurality of manipulation wires respectively engage with the sliding parts, and wherein the plurality of sliding parts become slidable individually when the bending manipulation part transits from the retracted position to the manipulation position.

(7) The catheter according to any one of the above (2) to (6), wherein the manipulation-part main body further includes a pulling restricting part, and wherein the pulling restricting part restricts that the bending manipulation part at the retracted position applies the pulling force to the manipulation wires.

(8) The catheter according to the above (7), wherein the pulling restricting part is latched to the bending manipulation part so as to restrict the pulling manipulations.

(9) The catheter according to the above (7) or (8), wherein the restriction of the pulling restricting part is released when the bending manipulation part transits from the retracted position to the manipulation position.

(10) The catheter according to any one of the above (2) to (9), wherein the bending manipulation part or the manipulation-part main body further includes a transition restricting part, and wherein the transition restricting part restricts the transition of the bending manipulation part from the manipulation position to the retracted position.

(11) The catheter according to any one of the above (2) to (10), wherein the coefficient of linear expansion of the tubular main body is greater than the coefficient of linear expansion of the manipulation wires.

(12) The catheter according to any one of the above (2) to (11), wherein the swelling coefficient of the tubular main body is greater than the swelling coefficient of the manipulation wires.

(13) The catheter according to any one of the above (1) to (12), wherein the tubular main body includes a main lumen, and a plurality of sub-lumens having a smaller diameter than the main lumen, and having the plurality of manipulation wires inserted therethrough, respectively.

(14) A catheter manipulation part used for a catheter which includes an elongated flexible tubular main body and a plurality of manipulation wires inserted through the tubular main body and having tips connected to a distal part of the tubular main body, in which the distal part of the tubular main body is bent by pulling the manipulation wires, the catheter manipulation part comprising: a manipulation-part main body mounted on a base end of the tubular main body; and a bending manipulation part including an engagement part engaging with base ends of the manipulation wires, and individually applying pulling force to the plurality of manipulation wires through pulling operations, wherein the bending manipulation part is provided so as to be movable with respect to the manipulation-part main body, and wherein the path lengths of the plurality of manipulation wires from the tips thereof to the engagement part are simultaneously increased or decreased when the bending manipulation part and the manipulation-part main body move relative to each other.

(15) A catheter manufacturing method for manufacturing the catheter according to any one of the above (2) to (13), comprising: a step of preparing the catheter in which the bending manipulation part is at the retracted position; a step of housing the catheter in a sterilizing package to heat and sterilize the catheter; and a step of causing the bending manipulation part in the heated and sterilized catheter to transit from the retracted position to the manipulation position, thereby removing some or all of loosening of the manipulation wires.

REFERENCE SIGNS LIST

10: TUBULAR MAIN BODY
11: PULL-IN POSITION
14: FIRST MARKER
16: SECOND MARKER
20: MAIN LUMEN
22: INNER LAYER
24: REINFORCING WIRE
26: WIRE REINFORCING LAYER
28: SUB-TUBE
30, 30a, 30b: MANIPULATION WIRE
32: SUB-LUMEN
34: FIRST OUTER LAYER
36: SECOND OUTER LAYER
38: OUTER LAYER
40: SECOND REINFORCING LAYER
42: SECOND REINFORCING WIRE
50: CATHETER MANIPULATION PART (MANIPULATION PART)
60: BENDING MANIPULATION PART
61: DIAL MANIPULATION PART
61a: EXTENDING RECESS
61b: ANNULAR GROOVE

61c: OPENING
62: LIMITER MEMBER
62a: SPRING ENGAGEMENT PART
62b: SHAFT PART
62c: LOCKING PROTRUSION
63: ENGAGING MEMBER
63a: IRREGULAR PART
63b: RECESSED CUTOUT
64: WIRE FIXING DISK
64a: SLIT
64b: FLANGE
64c: WINDING PART
64d: PROJECTION
65: SHAFT MEMBER
65a: ROTATING SHAFT
65b, 65c: GUIDE RIB
66: ENGAGEMENT PART
68: TRANSITION RESTRICTING PART
70: HUB CONNECTOR
72: REINFORCING RIB
73: PIN HOLE
75: TIP OPENING
77: MOUNTING PORT
80: MANIPULATION-PART MAIN BODY
81: SEPARATION SURFACE
82: UPPER MAIN BODY
82a: UPPER RECESS
82b: INSERTION PROTRUSION
82c: PIN HOLE
82d, 84d: RECESSED GROOVE
84: LOWER MAIN BODY
84a: LOWER RECESS
84b: REAR END
84c: PIN
84g: RETRACTION-SIDE GAP
84h: MANIPULATION-SIDE GAP
84i: INTERMITTENT RIB
84j: INNER GUIDE
85: ENGAGEMENT PART
87: PROTECTOR
88: LOCK SLIDER
89: PULLING RESTRICTING PART
90: REINFORCING MEMBER
92: OPENING
100: CATHETER
110, 120: SLIDING PART
111: ENGAGING PROTRUSION
112: SLIDING RING
131: CLAW
132: LOCKING PIECE
133: SLIDING GROOVE
134: SLIDING PROJECTION
DE: DISTAL PART
PE: BASE END

The invention claimed is:

1. A catheter, comprising:
an elongated flexible tubular main body;
a plurality of manipulation wires inserted through the tubular main body and having tips connected to a distal part of the tubular main body;
a manipulation-part main body provided at a base end of the tubular main body; and
a bending manipulation part having an engagement part configured to engage with base ends of the manipulation wires, and individually apply pulling force to the plurality of manipulation wires through a pulling operation to bend the distal part of the tubular main body,
wherein the bending manipulation part is provided such that the bending manipulation part is capable of transiting to a manipulation position or a retracted position with respect to the manipulation-part main body, and configured such that path lengths of the manipulation wires when the bending manipulation part is at the retracted position are shorter than the path lengths when the bending manipulation part is at the manipulation position, and that when the bending manipulation part at the manipulation position performs the pulling operation, the pulling force is applied to the plurality of manipulation wires and the distal part of the tubular main body is bent, the manipulation-part main body further comprises a pulling restricting part configured to restrict the bending manipulation part from applying the pulling force to the manipulation wires when the bending manipulation part is at the retracted position, the restriction of the pulling restricting part is released when the bending manipulation part transits from the retracted position to the manipulation position, the bending manipulation part is rotatable with respect to the manipulation-part main body, and the pulling restricting part is positioned to be fitted to a structure formed in the bending manipulation part such that the bending manipulation part at the retracted position does not cause the pulling operation.

2. The catheter according to claim 1, wherein the manipulation position and the retracted position are positioned side by side in an axial direction of the tubular main body.

3. The catheter according to claim 1, wherein the engagement part of the bending manipulation part is provided in a plurality, the base ends of the plurality of manipulation wires are configured to respectively engage with the engagement parts, and the plurality of engagement parts are integrally movable when the bending manipulation part transits from the retracted position to the manipulation position.

4. The catheter according to claim 1, wherein the bending manipulation part is configured such that a first manipulation wire of the manipulation wires is tensioned and a second manipulation wire of the manipulation wires is loosened when the bending manipulation part is rotated in one direction, and that the second manipulation wire is tensioned and the first manipulation wire is loosened when the bending manipulation part is rotated in another direction.

5. The catheter according to claim 1, wherein the bending manipulation part or the manipulation-part main body further comprises a transition restricting part, and the transition restricting part is configured to restrict transition of the bending manipulation part from the manipulation position to the retracted position.

6. The catheter according to claim 1, wherein the tubular main body has a coefficient of linear expansion which is greater than a coefficient of linear expansion of the manipulation wires.

7. The catheter according to claim 1, wherein the tubular main body has a swelling coefficient which is greater than a swelling coefficient of the manipulation wires.

8. The catheter according to claim 1, wherein the tubular main body comprises a main lumen, and a plurality of sub-lumens having a diameter smaller than a diameter of the main lumen, and having the plurality of manipulation wires inserted therethrough, respectively.

9. A method for manufacturing the catheter of claim 1, comprising:
preparing the catheter in which the bending manipulation part is at the retracted position;

housing the catheter in a sterilizing package such that the catheter is heated and sterilized; and causing the bending manipulation part in the heated and sterilized catheter to transit from the retracted position to the manipulation position such that some or all of loosening of the manipulation wires is removed.

10. The catheter according to claim 2, wherein the engagement part of the bending manipulation part is provided in a plurality, the base ends of the plurality of manipulation wires are configured to respectively engage with the engagement parts, and the plurality of engagement parts are integrally movable when the bending manipulation part transits from the retracted position to the manipulation position.

11. The catheter according to claim 10, wherein the bending manipulation part is configured such that a first manipulation wire of the manipulation wires is tensioned and a second manipulation wire of the manipulation wires is loosened when the bending manipulation part is rotated in one direction, and that the second manipulation wire is tensioned and the first manipulation wire is loosened when the bending manipulation part is rotated in another direction.

12. The catheter according to claim 2, wherein the bending manipulation part or the manipulation-part main body further comprises a transition restricting part, and the transition restricting part is configured to restrict transition of the bending manipulation part from the manipulation position to the retracted position.

13. The catheter according to claim 2, wherein the tubular main body has a coefficient of linear expansion which is greater than a coefficient of linear expansion of the manipulation wires.

14. The catheter according to claim 2, wherein the tubular main body has a swelling coefficient which is greater than a swelling coefficient of the manipulation wires.

15. The catheter according to claim 2, wherein the tubular main body comprises a main lumen, and a plurality of sub-lumens having a diameter smaller than a diameter of the main lumen, and having the plurality of manipulation wires inserted therethrough, respectively.

16. The catheter according to claim 5, wherein the bending manipulation part is sandwiched between an upper main body and a lower main body of the manipulation-part main body, and the bending manipulation part comprises the transition restricting part which is shaped such that when the transition restricting part is fitted to a gap formed in the lower main body, the bending manipulation part does not transit from the manipulation position to the retracted position.

17. The catheter according to claim 1, wherein the structure formed in the bending manipulation part is a recess or a projection.

18. A catheter manipulation part for a catheter, comprising:
 a manipulation-part main body mounted on a base end of an elongated flexible tubular main body of a catheter; and
 a bending manipulation part comprising an engagement part configured to engage with base ends of a plurality of manipulation wires of the catheter, and individually apply pulling force to the plurality of manipulation wires through pulling operations,
wherein the catheter comprises the tubular main body and the plurality of manipulation wires inserted through the tubular main body and having tips connected to a distal part of the tubular main body, and in which the distal part of the tubular main body is bent by pulling the manipulation wires, the bending manipulation part is provided such that the bending manipulation part is capable of transiting to a manipulation position or a retracted position with respect to the manipulation-part main body, and configured such that path lengths of the manipulation wires when the bending manipulation part is at the retracted position are shorter than the path lengths when the bending manipulation part is at the manipulation position, and that when the bending manipulation part at the manipulation position performs the pulling operation, the pulling force is applied to the plurality of manipulation wires and the distal part of the tubular main body is bent, the manipulation-part main body further comprises a pulling restricting part configured to restrict the bending manipulation part from applying the pulling force to the manipulation wires when the bending manipulation part is at the retracted position, the restriction of the pulling restricting part is released when the bending manipulation part transits from the retracted position to the manipulation position, the bending manipulation part is rotatable with respect to the manipulation-part main body, and the pulling restricting part is positioned to be fitted to a structure formed in the bending manipulation part such that the bending manipulation part at the retracted position does not cause the pulling operation.

* * * * *